(12) United States Patent
Eber et al.

(10) Patent No.: US 10,501,768 B2
(45) Date of Patent: Dec. 10, 2019

(54) METHOD OF PRODUCING RNA FROM CIRCULAR DNA AND CORRESPONDING TEMPLATE DNA

(71) Applicant: CureVac AG, Tübingen (DE)

(72) Inventors: Fabian Johannes Eber, Tübingen (DE); Stefanie Sewing, Tübingen (DE); Wenke Wagner, Reutlingen (DE)

(73) Assignee: CureVac AG, Tübingen (DE)

( * ) Notice: Subject to any disclaimer, the term of this patent is extended or adjusted under 35 U.S.C. 154(b) by 0 days.

(21) Appl. No.: 15/743,988

(22) PCT Filed: Jul. 13, 2016

(86) PCT No.: PCT/EP2016/066649
§ 371 (c)(1),
(2) Date: Jan. 11, 2018

(87) PCT Pub. No.: WO2017/009376
PCT Pub. Date: Jan. 19, 2017

(65) Prior Publication Data
US 2018/0201967 A1    Jul. 19, 2018

(30) Foreign Application Priority Data
Jul. 13, 2015 (WO) ................ PCT/EP2015/065999

(51) Int. Cl.
*C12P 19/34* (2006.01)
*C12Q 1/6865* (2018.01)
*C12N 15/52* (2006.01)

(52) U.S. Cl.
CPC ............. *C12P 19/34* (2013.01); *C12N 15/52* (2013.01); *C12Q 1/6865* (2013.01)

(58) Field of Classification Search
CPC ....................................................... C12P 19/34
See application file for complete search history.

(56) References Cited

U.S. PATENT DOCUMENTS

| | | |
|---|---|---|
| 2003/0087241 A1 | 5/2003 | Kool |
| 2005/0032730 A1 | 2/2005 | Von der Mulbe et al. |
| 2005/0059624 A1 | 3/2005 | Hoerr et al. |
| 2005/0250723 A1 | 11/2005 | Hoerr et al. |
| 2005/0287539 A1* | 12/2005 | Labourier ............... C12N 15/79 435/6.11 |
| 2006/0188490 A1 | 8/2006 | Hoerr et al. |
| 2007/0099296 A1* | 5/2007 | Parkin .................. C07K 14/005 435/345 |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0059344 A1* | 3/2013 | Striedner ............... C12N 15/70 435/91.32 |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |

(Continued)

FOREIGN PATENT DOCUMENTS

| | | |
|---|---|---|
| WO | WO 2014/152027 | 9/2014 |
| WO | WO 2014/186334 | 11/2014 |

(Continued)

OTHER PUBLICATIONS

Gavin et al. (The Journal of Biological Chemistry 272: 1461-1472 (Year: 1997).*
Fechter et al. FEBS Letters 436:99-103 (Year: 1998).*
Schurer et al. Nucleic Acid Res. 20(12)e56, pp. 1-5 (Year: 2002).*
H. Nielsen (Ed.) RNA. Methods in Molecular Biology 703 Springer, Chapter 3 Beckert et al. Synthesis of RNA by in vitro transcription, pp. 29-41 (Year: 2011).*
Chowira et al., "In vitro and in vivo comparison of hammerhead, hairpin, and hepatitis delta virus self-processing ribozyme cassettes. ," *J. Biol. Chem.*, 269(41):25856-25864, 1994.

(Continued)

*Primary Examiner* — Brian Whiteman
(74) *Attorney, Agent, or Firm* — Parker Highlander PLLC

(57) ABSTRACT

The present invention is concerned with a method of producing a target RNA using a circular DNA, wherein said method does not comprise a step of linearizing said circular DNA. The present invention further relates to a circular DNA comprising an RNA polymerase promoter sequence, followed by a sequence encoding a target RNA, followed by a sequence encoding a self-cleaving ribozyme, followed by an RNA polymerase terminator sequence element, wherein the latter element may comprise several RNA polymerase terminator sequences. Multimeric DNA obtained by rolling circle amplification of said circular DNA is also within the scope of the present invention.

19 Claims, 8 Drawing Sheets
Specification includes a Sequence Listing.

(56) References Cited

U.S. PATENT DOCUMENTS

| | | |
|---|---|---|
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |

FOREIGN PATENT DOCUMENTS

| | | |
|---|---|---|
| WO | WO 2016-107877 | 7/2016 |
| WO | WO 2016-165825 | 10/2016 |
| WO | WO 2016-165831 | 10/2016 |
| WO | WO 2016-174227 | 11/2016 |
| WO | WO 2016-174271 | 11/2016 |
| WO | WO 2016-184575 | 11/2016 |
| WO | WO 2016-184576 | 11/2016 |
| WO | WO 2016-193206 | 12/2016 |
| WO | WO 2016-193226 | 12/2016 |
| WO | WO 2016-203025 | 12/2016 |
| WO | WO 2017-001058 | 1/2017 |
| WO | WO 2017-021546 | 2/2017 |
| WO | WO 2017-025120 | 2/2017 |
| WO | WO 2017-025447 | 2/2017 |
| WO | WO 2017-036580 | 3/2017 |
| WO | WO 2017/064146 | 4/2017 |
| WO | WO 2017/081110 | 5/2017 |

OTHER PUBLICATIONS

Daubendiek et al., "Generation of catalytic RNAs by rolling transcription of synthetic DNA nanocircles," *Nat. Biotechnol.*, 15:273-277, 1997.

Diegelman et al., "Generation of circular RNAs and trans-cleaving catalytic RNAs by rolling transcription of circular DNA oligonucleotides encoding hairpin ribozymes," *Nucleic Acids Res.*, 26(13):3235-3241, 1998.

Du et al., "Engineering multigene expression in vitro and in vivo with small terminators for T7 RNA polymerase," *Biotechnol. Bioeng.*, 104(6):1189-1196, 2009.

Ferre-D'Amare et al., "Use of Cis- and Trans-Ribozymes to Remove 5' and 3' Heterogeneities From Milligrams of In Vitro Transcribed RNA," *Nucleic Acids Res.*, 977-978, 1996.

International Preliminary Report on Patentability issued in corresponding PCT Application No. PCT/EP2016/066649, dated Sep. 27, 2016.

International Search Report and Written Opinion issued in corresponding PCT Application No. PCT/EP2016/066649, dated Sep. 27, 2016.

Kieft, "A general method for rapid and nondenaturing purification of RNAs," RNA, 10(6):988-995, 2004.

Lyakhov et al., "Pausing and termination by bacteriophage T7 RNA polymerase1," *J. Mol. Biol.*, 280(2):201-213, 1998.

Price et al., "Crystallization of RNA-protein complexes I. Methods for the large-scale preparation of RNA suitable for crystallographic studies," *J. Mol. Biol.*, 249(2):398-408, 1995.

* cited by examiner

METHOD OF PRODUCING RNA FROM CIRCULAR DNA AND CORRESPONDING TEMPLATE DNA

This application is a national phase application under 35 U.S.C. § 371 of International Application No. PCT/EP2016/066649, filed Jul. 13, 2016, which claims benefit of International Application No. PCT/EP2015/065999, filed Jul. 13, 2015, the entire contents of each of which are hereby incorporated by reference.

FIELD OF THE INVENTION

The present invention relates to a method of producing a target RNA, wherein said method does not comprise a step of linearizing a circular DNA that is provided in a step of the method. The present invention further relates to a circular DNA comprising specific sequence elements as described herein and to a multimeric DNA obtained by rolling circle amplification of the afore-mentioned circular DNA. Finally, several uses as described herein are part of the present invention.

BACKGROUND OF THE INVENTION

Ribonucleic acid (RNA) molecules have gained much attention over the last years, particularly in the medical field. Thus, therapeutic RNA molecules represent a promising class of drugs, wherein RNA-based therapeutics include mRNA molecules encoding antigens for use as vaccines (Fotin-Mleczek et al. (2012) J. Gene Med. 14(6): 428-439). In addition, it is envisioned to use RNA molecules for replacement therapies, e.g. by providing missing proteins such as growth factors or enzymes to patients (Karikó et al. (2012) Mol. Ther. 20(5):948-953; Kormann et al. (2012) Nat. Biotechnol. 29(2):154-157, Thess et al. (2015) Mol. Ther. doi: 10.1038/mt.2015.103). Furthermore, the therapeutic use of noncoding immunostimulatory RNA molecules (Heidenreich et al. (2014) Int J Cancer. December 21. doi: 10.1002/ijc.29402) and other non-coding RNAs such as microRNAs and long noncoding RNAs is considered (Esteller (2011) Nat. Rev. Genet. 15 12(12):861-74).

In view of the above, there is a permanent need for new methods of producing RNA, which result in a high yield of the RNA to be produced. Furthermore, the RNA has to be produced in a high quality, particularly if it is applied in the medical field. Cost-efficacy of such new methods is of course also an important factor. Accordingly, new methods are sought after in the field of RNA production, which on the one hand result in RNA in the desired yield and quality, and on the other hand are economical in terms of the number of steps, the complexity of the steps, and the resources used in the steps.

WO 2012/170433 in the name of Sutro Biopharma, Inc. discloses means to transcribe circular plasmid DNA into either tRNA or mRNA. The method disclosed therein involves the use of multiple DNA:RNA polymerase termination sequences to prevent waste of high energy phosphates due to inefficient termination of the polymerases, wherein the focus in WO 2012/170433 is on polymerase termination sequences (or elements) comprising at least one Class I termination sequence in combination with at least one Class II termination sequence. WO 2012/170433 is in particular concerned with the production of tRNA, see claim 1 of WO 2012/170433.

WO 2014/186334 in the name of Robert Kruse discloses a method of producing a circular RNA, preferably circular mRNA, wherein the underlying DNA vector comprises two elements flanking the sequence of interest, namely a self-circularizing intron 5' slice junction and a self-circularizing intron 3' slice junction resulting in self-circularization of the RNA after transcription. The DNA vector may optionally contain an RNA polymerase terminator sequence.

SUMMARY OF THE INVENTION

The present invention solves the above need, inter alia by providing a new cost-efficient method of producing RNA. Further, a circular DNA comprising specific sequence elements as outlined in detail below is provided herein.

In a first aspect, the present invention is directed to a method of producing a target RNA comprising the steps of:
a) providing a circular DNA as template DNA comprising the following sequence elements from 5' to 3':
  i. an RNA polymerase promoter sequence operably linked to
  ii. a sequence encoding said target RNA operably linked to
  iii. a sequence encoding a self-cleaving ribozyme, wherein said self-cleaving ribozyme cleaves close to or at its 5' end, operably linked to
  iv. an RNA polymerase terminator sequence element; and
b) in vitro transcription of said template DNA to obtain said target RNA;
c) purifying said target RNA by at least one purification step in order to obtain purified target RNA;
wherein said method does not comprise a step of linearizing said circular DNA provided in step a).

It is noted that said self-cleaving ribozyme referred to in step a) iii. of the first aspect of the present invention fails to catalyze a self-circularization of the resulting RNA. Put in different words, the circular DNA provided as template DNA in step a) of the method of the first aspect of the present invention fails to comprise a counterpart sequence to the sequence referred to under iii. located upstream of the sequence referred to under ii. Such a counterpart sequence may be referred to as "self circularizing intron 5' splice junction" or "5' splice junction" or "sequence encoding a 5' splice junction" or "counterpart upstream of the sequence of interest".

Accordingly, the produced target RNA according to the first aspect of the invention is a linear target RNA.

In a preferred embodiment, the in vitro transcription in step b) is carried out in the presence of a DNA dependent RNA polymerase selected from the group consisting of T3 RNA polymerase, T7 RNA polymerase and SP6 RNA polymerase, wherein T7 RNA polymerase is particularly preferred. If the in vitro transcription is carried out in the presence of T7 RNA polymerase, it is preferred that the circular DNA comprises a T7 RNA polymerase promoter sequence.

In another preferred embodiment, said circular DNA is at least partially a circular supercoiled DNA. Said circular DNA may be circular plasmid DNA, wherein said plasmid DNA comprises a sequence suitable for multiplication of the plasmid, preferably an origin of replication, and preferably a selection marker. In a particularly preferred embodiment, said circular DNA is a circular DNA according to the second aspect of the invention described below including of course any of the embodiments thereof disclosed herein.

In a further preferred embodiment, the method comprises in step b) a step of enzymatically capping the RNA. As an alternative to this preferred embodiment, the in vitro transcription in step b) is carried out in the presence of a cap analog. Said cap analog is preferably selected from the group consisting of N7-MeGpppG (=m7G(5')ppp(5')G), m7G(5')ppp(5')A, ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. Further cap analoga are described below.

In a preferred embodiment, the in vitro transcription in step b) is carried out in the presence of naturally occurring nucleotides and/or optionally in the presence of at least one modified nucleotide.

If the target RNA is co-transcriptionally capped, the in vitro transcription in step b) is preferably carried out in presence of a cap analog, GTP, ATP, CTP and UTP (naturally occurring nucleotides and/or optionally in the presence of at least one modified nucleotide), wherein the amount of GTP is preferably reduced with respect to the amounts of ATP, CTP and UTP. More preferably, the ratio of the cap analog to GTP is then in a range from 10:1 to 1:1.

It can be preferred to carry out the in vitro transcription in step b) in the presence of naturally occurring nucleotides and at least one modified nucleotide, wherein said at least one modified nucleotide at least partially replaces at least one naturally occurring nucleotide. Also in this case, the method may comprise a step of enzymatically capping the RNA in step b) or carrying out the in vitro transcription in step b) in the presence of a cap analog (see above).

If at least one modified nucleotide is used, it is preferred to carry out the in vitro transcription in step b) in the presence of a cap analog. It can be preferred that said at least one modified nucleotide is selected from the group consisting of 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate and puromycin-5'-triphosphate, xanthosine-5'-triphosphate. Further modified nucleotides are described below.

In another preferred embodiment, the at least one purification step in step c) comprises at least one step selected from the group consisting of a precipitation step, a tangential flow filtration step and a chromatographic step. It can be preferred that the precipitation step is an alcoholic precipitation step or a LiCl precipitation step. It can further be preferred that the tangential flow filtration step is a diafiltration step using tangential flow filtration and/or a concentration step using tangential flow filtration. Finally, it can be preferred that the chromatographic step is selected from the group consisting of HPLC, anion exchange chromatography, affinity chromatography, hydroxyapatite chromatography and core bead chromatography.

In a particularly preferred embodiment, said target RNA is purified in step c) by at least one first and at least one second purification step.

In one embodiment thereof, it can be preferred that the at least one first purification step comprises a precipitation step and the at least one second purification step comprises a chromatographic step. More preferably, the at least one first purification step comprises an alcohol precipitation step or a LiCl precipitation step and the at least one second purification step comprises a chromatographic step selected from the group consisting of HPLC, anion exchange chromatography, affinity chromatography, hydroxyapatite chromatography and core bead chromatography. Most preferably, the at least one first purification step comprises a LiCl precipitation step and the at least one second purification step comprises a step of RP-HPLC.

In an alternative embodiment thereof, it can be preferred that the at least one first purification step comprises a tangential flow filtration step and the at least one second purification step comprises a chromatographic step. More preferably, the at least one first purification step comprises a diafiltration step using tangential flow filtration and/or a concentration step using tangential flow filtration and the at least one second purification step comprises a chromatographic step selected from the group consisting of HPLC, anion exchange chromatography, affinity chromatography, hydroxyapatite chromatography and core bead chromatography. Most preferably, the at least one first purification step comprises a diafiltration step using tangential flow filtration and the at least one second purification step comprises a step of RP-HPLC.

In any of the above embodiments relating to at least two purification steps, it is preferred that the at least one first purification step is carried out prior to the at least one second purification step.

In another preferred embodiment, said circular DNA is provided in step a) and then amplified in an additional step by rolling circle amplification prior to the in vitro transcription in step b). In this embodiment, the circular DNA is provided in step a) in a concentration or amount that makes it not suitable as template DNA for production of a target RNA in the desired yield and/or quality. Therefore, an amplification step is necessary to amplify said circular DNA such that it is provided in step b) at a concentration or amount that is suitable as template DNA for production of a target RNA in the desired yield and/or quality, wherein this amplification step is carried out by rolling circle amplification. Said amplified template DNA may be purified prior to the in vitro transcription of step b) by any common DNA purification step, preferably by DNA extraction and/or precipitation. In this embodiment, the circular DNA is, prior to its provision in step a), not subject to an amplification reaction for the purpose of the method claimed herein. This in particular refers to a situation, where the circular DNA is, for the purpose of producing a target RNA according to the present invention, not amplified using either i) fermentative proliferation and subsequent isolation from bacteria or ii) PCR-methods using specific primers and thermal cycling prior to providing it in step a).

In an alternative embodiment to the above, said method does not comprise a step of amplifying said circular DNA after providing the circular DNA in step a). In this case, said circular DNA is preferably provided in step a) at a concentration ranging from about 0.075 g/L to about 0.3 g/L, preferably from about 0.1 g/L to about 0.2 g/L. It is particularly preferred to provide said circular DNA at a concentration of about 0.15 g/L. In this embodiment, the circular DNA may be a plasmid DNA, which is preferably amplified before carrying out the method disclosed herein, i.e. prior to providing it in step a), by fermentative proliferation and subsequent isolation from bacteria. The circular DNA may also be circular DNA lacking an origin of replication and/or resistance genes, which is preferably amplified before carrying out the method disclosed herein, i. e. prior to providing it in step a), by PCR-methods using specific primers and thermal cycling followed by a method of circularization such as intramolecular ligation.

In a second aspect, the present invention is directed to a circular DNA comprising the following sequence elements from 5' to 3':
  a) an RNA polymerase promoter sequence operably linked to
  b) a sequence encoding a target RNA operably linked to
  c) a sequence encoding a self-cleaving ribozyme, wherein said self-cleaving ribozyme cleaves close to or at its 5' end, operably linked to
  d) an RNA polymerase terminator sequence element.

It is noted that said self-cleaving ribozyme referred to in step c) of the second aspect of the present invention fails to catalyze a self-circularization of the resulting RNA.

This may additionally or alternatively be expressed in that the circular DNA according to the second aspect of the present invention fails to comprise a counterpart sequence to the sequence referred to under c) located upstream of the sequence referred to under b). Such a counterpart sequence may be referred to as "self circularizing intron 5' splice junction" or "5' splice junction" or "sequence encoding a 5' splice junction" or "counterpart upstream of the sequence of interest". In an embodiment, the second aspect is thus directed to a circular DNA comprising the following sequence elements from 5' to 3':
  a) an RNA polymerase promoter sequence operably linked to
  b) a sequence encoding a target RNA operably linked to
  c) a sequence encoding a self-cleaving ribozyme, wherein said self-cleaving ribozyme cleaves close to or at its 5' end, operably linked to
  d) an RNA polymerase terminator sequence element,
wherein said circular DNA does not comprise a ribozyme sequence upstream of sequence element b). Put in other words, said circular DNA does not comprise a ribozyme-related sequence (such as in particular a splice junction) upstream of sequence element b). Still put in other words, said circular DNA does not comprise a self circularizing intron 5' splice junction; or a 5' splice junction; or a sequence encoding a 5' splice junction; or a ribozyme counterpart upstream of sequence element b).

In an embodiment thereof, said circular DNA is at least partially a circular supercoiled DNA. Said circular DNA may be circular plasmid DNA, wherein said plasmid DNA comprises a sequence suitable for multiplication of the plasmid, preferably an origin of replication, and preferably a selection marker.

In another preferred embodiment, said RNA polymerase promoter sequence is selected from the group consisting of a T3 RNA polymerase promoter sequence, a T7 RNA polymerase promoter sequence and an SP6 polymerase promoter sequence. It is particularly preferred that said RNA polymerase promoter sequence is a T7 RNA polymerase promoter sequence.

In a further preferred embodiment, said self-cleaving ribozyme encoded in sequence element c) is selected from the group consisting of a hepatitis delta virus (HDV) ribozyme, a hammerhead ribozyme and a hairpin ribozyme. However, any sequence encoding a self-cleaving ribozyme with in cis activity cleaving close to its 5' end or at its 5' end may be used. It is noted that said self-cleaving ribozyme encoded in sequence element c) results in a 2'3' cyclic phosphate at the 3' end of the target RNA.

In yet another preferred embodiment, said RNA polymerase terminator sequence element comprises at least one RNA polymerase terminator sequence selected from a Class I termination sequence and a Class II termination sequence as defined below. It is particularly preferred that said RNA polymerase terminator sequence element comprises at least one Class II termination sequence. It is most preferred that said RNA polymerase terminator sequence element comprises at least one Class II termination sequence and does not comprise a Class I termination sequence.

Said at least one Class II termination sequence is preferably selected from the group consisting of the VSV terminator sequence, the PTH terminator sequence, the rrnB T1 downstream terminator sequence, the rrnC terminator sequence, the concatemer junction sequence of the replicating T7 DNA, and a variant of any of the foregoing.

A variant of the rrnB T1 downstream terminator sequence is preferably selected from the group consisting of the 1W1 terminator sequence, the 1W2 terminator sequence, the 1W3 terminator sequence, the 2W1 terminator sequence, the 3W1 terminator sequence, the 4W1 terminator sequence, the 2W7 terminator sequence, the 1I1 terminator sequence, the 1I3 terminator sequence, the 1J1 terminator sequence, the 5K1 terminator sequence, the 1N1 terminator sequence, the 1P10 terminator sequence, the 5Q10 terminator sequence, the 1R11 terminator sequence, the 1S11 terminator sequence, the 3Y8 terminator sequence, the 4Y9 terminator sequence and the 3Z8 terminator sequence.

In a particular preferred embodiment, said at least one Class II termination sequence is selected from the group consisting of the VSV terminator sequence, the rrnB T1 downstream terminator sequence, and variants of the rrnB T1 downstream terminator sequence selected from the group consisting of the 5Q10 terminator sequence, the 1R11 terminator sequence, the 3Y8 terminator sequence, the 4Y9 terminator sequence and the 3Z8 terminator sequence. It is most preferred that said at least one Class II termination sequence is selected from the VSV terminator sequence and the 1R11 variant rrnB T1 downstream terminator sequence.

In another preferred embodiment, said RNA polymerase terminator sequence element comprises at least two Class II termination sequences, wherein said at least two Class II termination sequences are optionally separated by a spacer sequence. Preferably, said at least two Class II termination sequences are independently selected from the group consisting of the VSV terminator sequence, the PTH terminator sequence, the rrnB T1 downstream terminator sequence, the rrnC terminator sequence, the concatemer junction sequence of the replicating T7 DNA, and a variant of any of the foregoing. Said Class II termination sequences may be identical and can preferably be VSV terminator sequences or 1R11 variant rrnB T1 downstream terminator sequences.

In an even preferred embodiment thereof, said RNA polymerase terminator sequence element comprises at least three Class II termination sequences, wherein said at least three Class II termination sequences are optionally separated by a spacer sequence. Preferably, said at least three Class II termination sequences are independently selected from the group consisting of the VSV terminator sequence, the PTH terminator sequence, the rrnB T1 downstream terminator sequence, the rrnC terminator sequence, the concatemer junction sequence of the replicating T7 DNA, and a variant of any of the foregoing. Said Class II termination sequences may be identical and can preferably be VSV terminator sequences or 1R11 variant rrnB T1 downstream terminator sequences.

In the most preferred embodiment thereof, said RNA polymerase terminator sequence element comprises at least four Class II termination sequences, wherein said at least four Class II termination sequences are optionally separated by a spacer sequence. Preferably, said at least four Class II termination sequences are independently selected from the group consisting of the VSV terminator sequence, the PTH terminator sequence, the rrnB T1 downstream terminator sequence, the rrnC terminator sequence, the concatemer junction sequence of the replicating T7 DNA, and a variant of any of the foregoing. Said Class II termination sequences may be identical and can preferably be VSV terminator sequences or 1R11 variant rrnB T1 downstream terminator sequences.

The afore-mentioned latter two embodiments are particularly preferred in a circular DNA to be used in the method according to the first aspect of the present invention.

In a preferred embodiment relating to the first and the second aspect, the target RNA is selected from the group consisting of mRNA, viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA). It is particularly preferred that said target RNA is mRNA or immunostimulatory RNA.

In a third aspect, the present application relates to a multimeric DNA obtained by rolling circle amplification of said circular DNA according to the second aspect.

In a fourth aspect, the present invention is directed to the use of a circular DNA described in the second aspect or of the multimeric DNA described in the third aspect in a method described in the first aspect.

In a fifth aspect, the present invention is directed to the use of a method according to the first aspect to obtain an RNA yield, which is at least about identical compared to the RNA yield obtained in a method of producing RNA using linear DNA template.

In a sixth aspect, the present invention is directed to the use of a method according to the first aspect to produce a target RNA comprising at least one modified nucleotide.

In a seventh aspect, the present invention is directed to the use of a method according to the first aspect to produce mRNA as target RNA, wherein said mRNA provides at least the expression capability of mRNA produced by a method not resulting in a 2'3' cyclic phosphate at the 3' end of the mRNA. A preferred method not resulting in a 2'3' cyclic phosphate at the 3' end of the mRNA is a method comprising a step of in vitro transcription using linearized DNA. An alternative preferred method not resulting in a 2'3' cyclic phosphate at the 3' end of the mRNA is a method not comprising a template DNA comprising a sequence encoding a self-cleaving ribozyme.

The present invention further discloses in an eight aspect a method of producing a target RNA comprising the steps of:

a) providing a circular DNA comprising the following sequence elements from 5' to 3':
  i. an RNA polymerase promoter sequence operably linked to
  ii. a sequence encoding said target RNA
  iii. at least one restriction site;
b) amplifying said circular DNA by rolling circle amplification to obtain multimeric DNA;
c) digesting said multimeric DNA obtained in step b) with at least one restriction enzyme recognizing the at least one restriction site to obtain linear template DNA;
d) in vitro transcription of said template DNA to obtain said target RNA;
e) purifying said target RNA by at least one purification step in order to obtain purified target RNA.

The preferred embodiments described above in the first aspect regarding the i) in vitro transcription step, ii) enzymatically capping the RNA, iii) the presence of at least one modified nucleotide, iv) the purification step and v) the target RNA also apply to the eight aspect. As regards the circular DNA provided in step a) of the method of the eight aspect, it is preferred that the at least one restriction site is outside the sequence encoding the target RNA (in other words: the at least one restriction site is not present in the sequence encoding the target RNA), and it is even more preferred that the at least one restriction site is present after the 3' end of the sequence encoding the target RNA, most preferably directly after the 3' end of the sequence encoding the target RNA. Accordingly, the produced target RNA according to the eight aspect of the invention is a linear target RNA.

In a ninth aspect, the present invention is concerned with a multimeric DNA obtained by rolling circle amplification of a circular DNA, wherein said circular DNA comprises the following sequence elements from 5' to 3':
  i. an RNA polymerase promoter sequence operably linked to
  ii. a sequence encoding a target RNA
  iii. at least one restriction site.

The preferred embodiments described above in the second aspect regarding the RNA polymerase promoter sequence and the target RNA also apply to the circular DNA described in the ninth aspect. As regards the circular DNA described in the ninth aspect, it is preferred that the at least one restriction site is outside the sequence encoding the target RNA (in other words: the at least one restriction site is not present in the sequence encoding the target RNA), and it is even more preferred that the at least one restriction site is present after the 3' end of the sequence encoding the target RNA, most preferably directly after the 3' end of the sequence encoding the target RNA.

In a tenth aspect, the present invention relates to the use of a multimeric DNA of the ninth aspect in a method of producing a target RNA, preferably in the method of the eighth aspect described above.

BRIEF DESCRIPTION OF THE DRAWINGS

The figures shown in the following are merely illustrative and shall describe the present invention in a further way. These figures shall not be construed to limit the present invention thereto.

Scheme of a circular construct (a) carrying a terminator sequence element (black) and a sequence encoding a self-cleaving ribozyme (grey) for the in vitro production of RNA from a circular DNA template. Intermediate RNA products (b) may be cleaved by a self-cleaving ribozyme to yield target RNA with homogenous ends (c).

Figure 2:
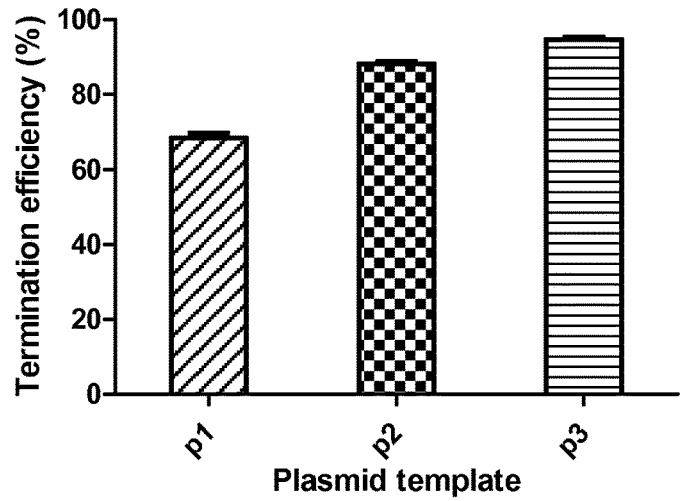

FIG. 2 Terminator sequences and termination efficiency

The termination efficiency of terminator sequence elements during in vitro transcriptions from linearized plasmids is shown for plasmids carrying a single VSV terminator (p1), one direct repeat of the 1R11 terminator sequence and a ribozyme (p2), or four repeats of the VSV terminator sequence including spacer sequences and a ribozyme (p3). The mean value of three transcription reactions was plotted together with the standard deviation indicated by the error bars.

Figure 3:
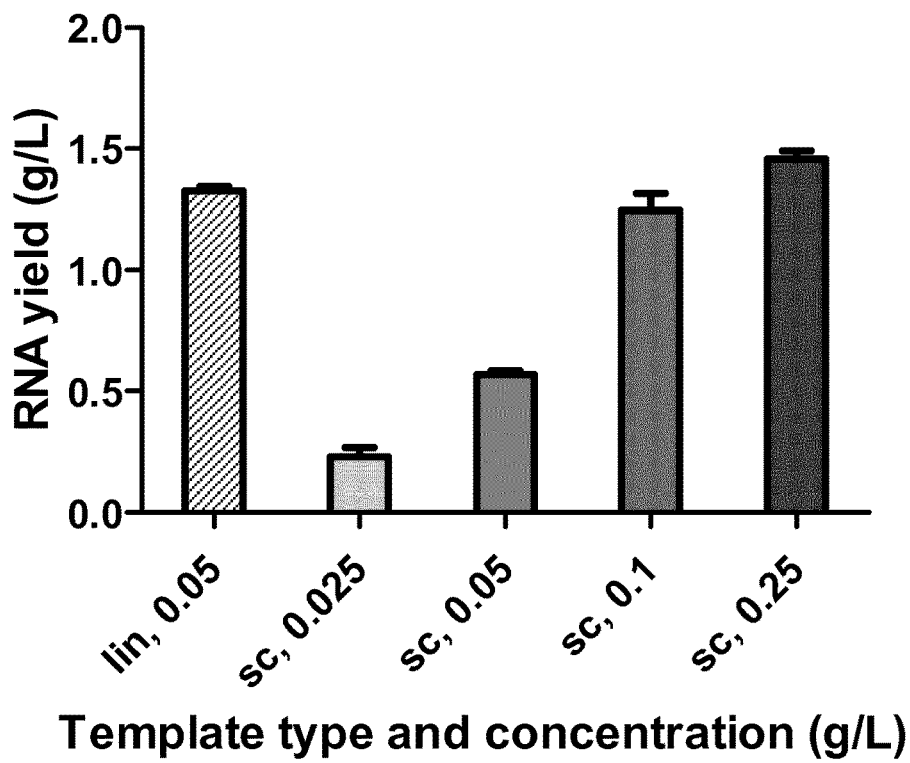

FIG. 3 RNA yield depending on template type and concentration

The yield of RNA from in vitro transcriptions with linear (lin) and supercoiled circular (sc) DNA templates (p3) is shown at template concentrations as indicated. The mean value of three transcription reactions was plotted together with the standard deviation indicated by the error bars.

Figure 4:
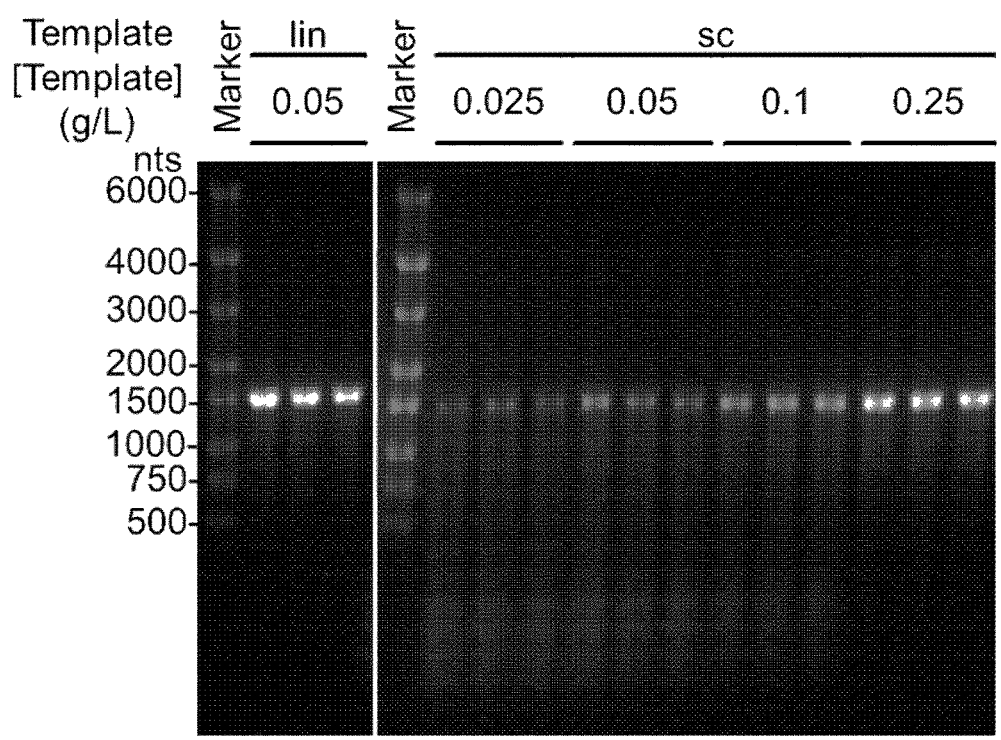

FIG. 4 RNA-composition after in vitro transcription using different templates

RNA obtained from in vitro transcriptions with linear (lin) or supercoiled circular (sc) DNA template (p3) at the template concentrations as indicated is shown in a denaturing agarose gel after electrophoresis.

Figure 5:
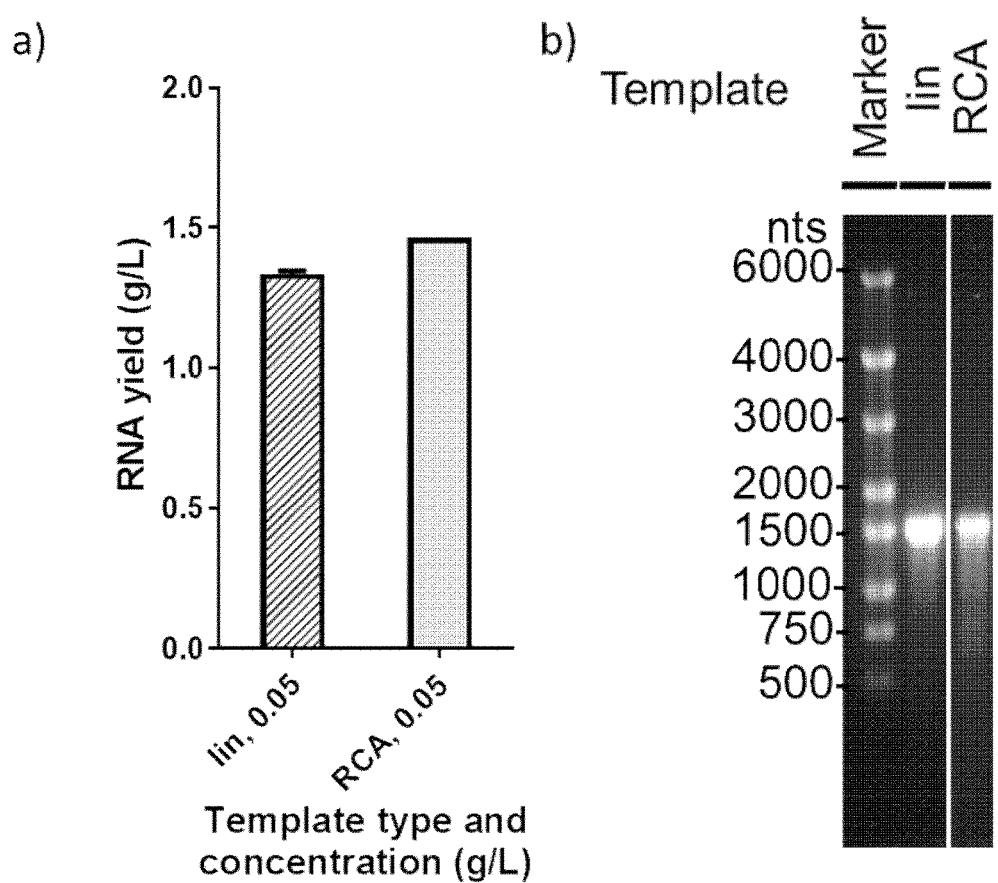

FIG. 5 RNA yield and RNA-composition using the product of rolling circle amplification (RCA) as DNA template In FIG. 5a), the yield of RNA from in vitro transcriptions with linear (lin) and RCA product (RCA) DNA templates (p3) is shown at a template concentration of 0.05 g/L. The mean value of three transcription reactions was plotted together with the standard deviation indicated by the error bars. FIG. 5b) shows RNA obtained from in vitro transcriptions with linear (lin) or RCA product (RCA) DNA template (p3) at a template concentration of 0.05 g/L in a denaturing agarose gel after electrophoresis.

Figure 6:
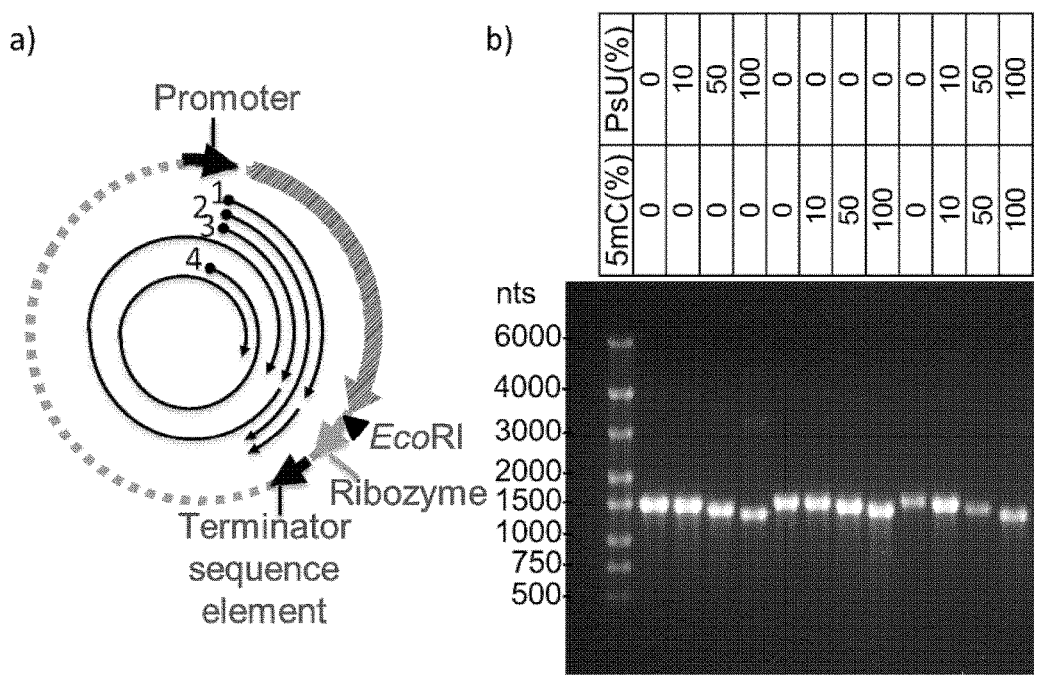

FIG. 6 Possible transcripts and the use of modified nucleotides

FIG. 6A shows possible transcripts from plasmid p3 for the in vitro production of RNA from a circular supercoiled DNA template. Situation 1: Termination and active ribozyme (1875 nts+~90-160 nts); Situation 2: Termination and inactive ribozyme (~1965-2035 nts); Situation 3: Read-through and active ribozyme (1875 nts+4098 nts); Situation 4: Read-through and inactive ribozyme (~6000 nts). FIG. 6B shows a gel electrophoretic analysis of RNA obtained by transcription from circular p3 with different percentages of PseudoUTP (pseudouridine-5'-triphosphate) (PsU) and/or 5-methyl CTP (5-methylcytidine-5'-triphosphate) (5mC) as indicated.

Figure 7:
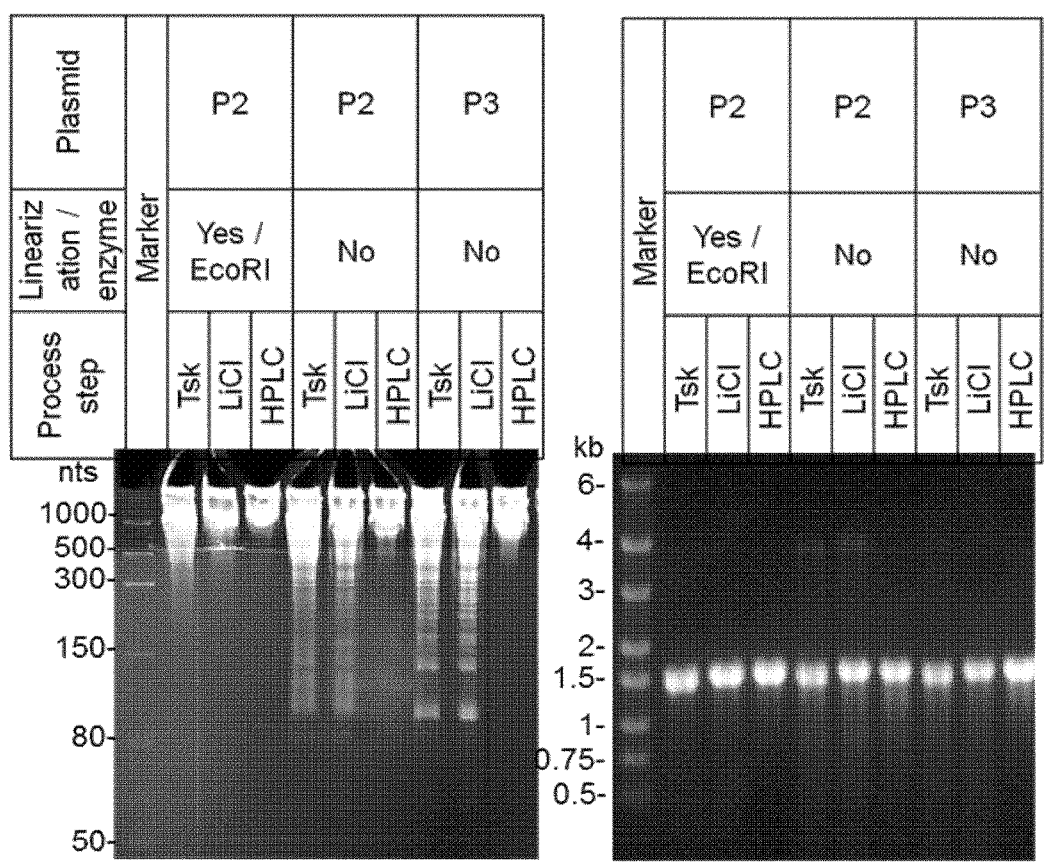

FIG. 7 RNA purification

Samples of different stages of the purification were analyzed on a 10% acrylamide/urea gel in TBE (left) and a 1.2% agarose/formaldehyde gel in MOPS buffer (right). RNA was either prepared using a linear plasmid or a circular plasmid as template DNA as indicated. 3.75 µg (left gel) and 1 µg (right gel) of each RNA preparation after transcription (Tsk), after subsequent precipitation with LiCl (LiCl), and after final HPLC separation (HPLC) were loaded on the gels.

Figure 8:
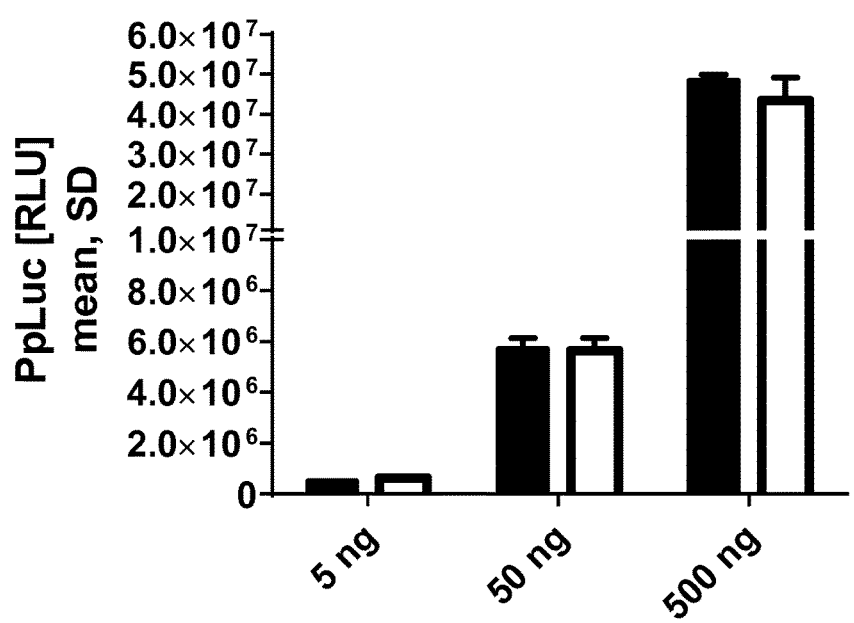

FIG. 8 RNA expression capability

FIG. 8 shows luciferase-expression in HeLa cells transfected with different amounts of RNA as indicated on the x-axis produced by in vitro transcription from circular (white bars) or linear (black bars) DNA template. Plasmid templates were EcoRI-linearized p3 (black bar) and circular p3-mod (white bar). The only difference between the transcripts from linearized p3 and p3-mod is the presence of a 2'3' cyclic phosphate at the 3' end of the RNA produced from circular p3-mod, which is not present in the RNA produced from linearized p3.

Figure 9:
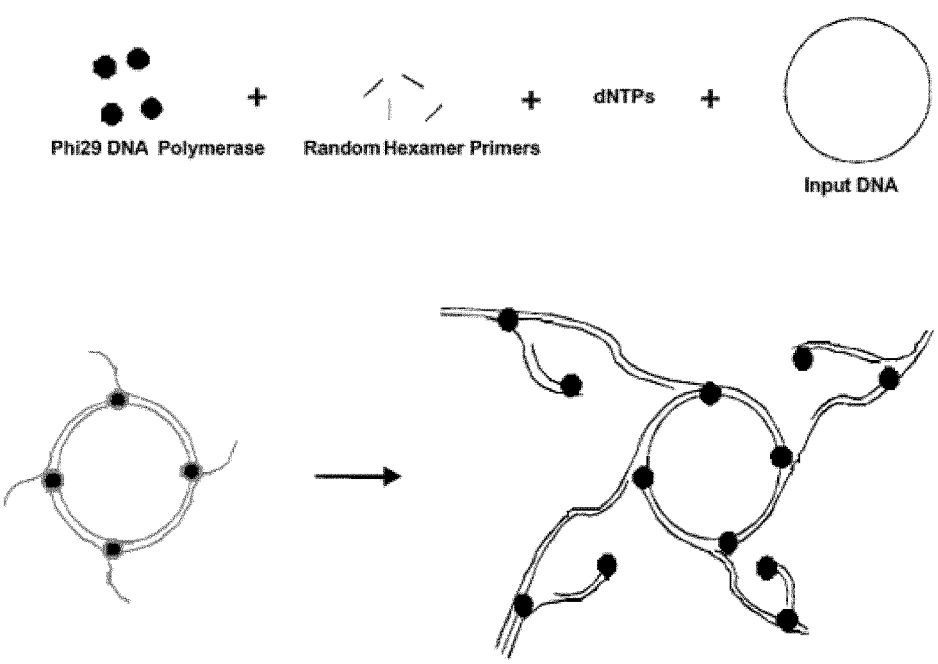

FIG. 9 Schematic depiction of RCA

FIG. 9 shows the scheme of the TempliPhi process in rolling circle amplification (RCA). This figure is taken from the instructions for the TempliPhi Amplification Kit by Amersham Biosciences.

DEFINITIONS

For the sake of clarity and readability the following definitions are provided. Any technical feature mentioned for these definitions may be read on each and every embodiment of the invention. Additional definitions and explanations may be specifically provided in the context of these embodiments.

As used in the specification and the claims, the singular forms of "a" and "an" also include the corresponding plurals unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

RNA: RNA is the usual abbreviation for ribonucleic acid. It is a nucleic acid molecule, i.e. a polymer consisting of nucleotide monomers. These nucleotides are usually adenosine-monophosphate, uridine-monophosphate, guanosine-monophosphate and cytidine-monophosphate monomers or analogs thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence. In addition to messenger RNA, several non-coding types of RNA exist which may be involved in regulation of transcription and/or translation, and immuno-stimulation. The term "RNA" further encompasses RNA molecules, such as viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA). An immunostimulatory RNA (isRNA) in the context of the invention may typically be a RNA that is able to induce an innate immune response. An isRNA usually does not have an open reading frame and thus does not provide a peptide-antigen, but elicits an innate immune response, e.g. by binding to pathogen-associated molecular patterns (PAMP) receptors (e.g. Toll-like-receptor (TLR) or other intracellular RNA sensors (e.g. RIG-I, MDA-5 or PKR).

DNA: DNA is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers or analogs thereof which are—by themselves—composed of a sugar moiety (deoxyribose), a base moiety and a phosphate moiety, and polymerize by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

In vitro transcription, template DNA, RNA polymerase promoter sequence: The term "in vitro transcription" relates to a process wherein RNA is synthesized in a cell-free system (in vitro). DNA is used as template for the generation of RNA transcripts. The promoter (also referred to herein as "promoter sequence") for controlling in vitro transcription can be any promoter for any DNA dependent RNA polymerase (referred to herein also as "RNA polymerase"). Particular examples of DNA dependent RNA polymerases are the T7, T3, and SP6 RNA polymerases. A DNA template for in vitro RNA transcription may be obtained by cloning of a nucleic acid, in particular cDNA corresponding to the target RNA to be in vitro transcribed, and introducing it into an appropriate DNA for in vitro transcription, for example into plasmid DNA. The cDNA may be obtained by reverse transcription of mRNA, chemical synthesis, or oligonucleotide cloning. Moreover, the DNA template for in vitro RNA synthesis may also be obtained by gene synthesis.

Methods for in vitro transcription are known in the art (Geall et al. (2013) Semin. Immunol. 25(2): 152-159; Brunelle et al. (2013) Methods Enzymol. 530:101-14). Reagents used in said method typically include:
1) a DNA template (as defined above) with a promoter sequence that has a high binding affinity for its respective RNA polymerase such as bacteriophage-encoded RNA polymerases;
2) ribonucleoside triphosphates (NTPs) for the four bases (adenine, cytosine, guanine and uracil);
3) optionally a cap analog as defined below (e.g. m7G(5') ppp(5')G (m7G));
4) a DNA-dependent RNA polymerase capable of binding to the promoter sequence within the DNA template (e.g. T7, T3 or SP6 RNA polymerase);
5) optionally a ribonuclease (RNase) inhibitor to inactivate any contaminating RNase;
6) optionally a pyrophosphatase to degrade pyrophosphate, which may inhibit transcription;
7) $MgCl_2$, which supplies $Mg^{2+}$ ions as a co-factor for the polymerase;
8) a buffer to maintain a suitable pH value, which can also contain antioxidants (e.g. DTT) and polyamines such as spermidine at optimal concentrations.

According to a preferred embodiment, the (transcription) buffer is selected from the group consisting of 4-(2-hydroxyethyl)-1-piperazineethanesulfonic acid (HEPES) and tris (hydroxymethyl)aminomethane (Tris). Preferably the buffer is used at a concentration from 10 to 100 mM, 10 to 75 mM, 10 to 50 mM, 10 to 40 mM, 10 to 30 mM or 10 to 20 mM. The pH value of the buffer can be adjusted with, for example, NaOH, KOH or HCl. Preferably the buffer has a pH value from 6 to 8.5, from 6.5 to 8.0, from 7.0 to 7.5, even more preferred 7.5. Most preferred is a buffer selected from the group consisting of 80 mM HEPES/KOH, pH 7.5 and 40 mM Tris/HCl, pH 7.5.

According to a preferred embodiment of the invention, the RNA polymerase is selected from the group consisting of T3, T7 and SP6 RNA polymerase. Preferably, the concentration of the RNA polymerase is from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. Even more preferred, the concentration of the RNA polymerase is from about 10 to 50 nM, 20 to 50 nM, or 30 to 50 nM. Most preferred is a RNA polymerase concentration of about 40 nM. The person skilled in the art will understand that the choice of the RNA polymerase concentration is influenced by the concentration of the DNA template. Therefore, in specific embodiments the concentration of the RNA polymerase is between 1 and 1000 U/µg template DNA, preferably between 10 and 100 U/µg DNA, particularly if plasmid DNA is used as template DNA.

In a typical assay outlined above, the concentration of linear DNA template is about 0.05 g/L. This concentration was found to be most efficient for the production of target RNA in the desired yield and quality.

According to a preferred embodiment of the invention, the in vitro transcription is performed in the presence of pyrophosphatase. Preferably, the concentration of the pyrophosphatase is from about 1 to 20 units/ml, 1 to 15 units/ml, 1 to 10 units/ml, 1 to 5 units/ml, or 1 to 2.5 units/ml. Even more preferred the concentration of the pyrophosphatase is about 5 units/ml.

According to a preferred embodiment of the invention, the in vitro transcription reaction mixture comprises $Mg^{2+}$ ions. Preferably, the $Mg^{2+}$ ions are provided in the form of $MgCl_2$ or $Mg(OAc)_2$. Preferably, the initial free $Mg^{2+}$ concentration is from about 1 to 100 mM, 1 to 75 mM, 1 to 50 mM, 1 to 25 mM, or 1 to 10 mM. Even more preferred the initial free $Mg^{2+}$ concentration is from about 10 to 30 mM or about 15 to 25 mM. Most preferred is an initial free $Mg^{2+}$ concentration of about 24 mM. The person skilled in the art will understand that the choice of the $Mg^{2+}$ concentration is influenced by the initial total NTP concentration.

According to a preferred embodiment of the invention, the in vitro transcription reaction mixture comprises a reducing agent (antioxidant) to keep the RNA polymerase in its active state. Preferably, the reducing agent is selected from the group consisting of dithiothreitol (DTT), dithioerythritol (DTE), Tris(2-carboxyethyl)phosphine (TCEP) and β-mercaptoethanol. Preferably the concentration of the reducing reagent is from about 1 to 50 mM, 1 to 40 mM, 1 to 30 mM, or 1 to 20 mM, or 1 to 10 mM. Even more preferred the concentration of the reducing reagent is from 10 to 50 mM or 20 to 40 mM. Most preferred is a concentration of 40 mM of DTT.

According to a preferred embodiment of the invention, the in vitro transcription reaction mixture comprises a polyamine. Preferably, the polyamine is selected from the group consisting of spermine and spermidine. Preferably the concentration of the polyamine is from about 1 to 25 mM, 1 to 20 mM, 1 to 15 mM, 1 to 10 mM, 1 to 5 mM, or about 1 to 2.5 mM. Even more preferred the concentration of the polyamine is about 2 mM. Most preferred is a concentration of 2 mM of spermidine.

According to a preferred embodiment of the invention, the in vitro transcription reaction mixture comprises a ribonuclease inhibitor. Preferably, the concentration of the ribonuclease inhibitor is from about 1 to 500 units/ml, 1 to 400 units/ml, 1 to 300 units/ml, 1 to 200 units/ml, or 1 to 100 units/ml. Even more preferred the concentration of the ribonuclease inhibitor is about 200 units/ml.

According to a preferred embodiment of the invention, the total NTP concentration in the in vitro transcription reaction mixture is between 1 and 100 mM, preferably between 10 and 50 mM, and most preferably between 10 and 20 mM.

According to the invention, the term total nucleotide concentration means the total concentration of NTPs, e.g. the sum of the concentrations of ATP, GTP, CTP, UTP, and/or cap analog present initially in the in vitro transcription when the various components of the reaction have been assembled in the final volume for carrying out the in vitro transcription reaction. Naturally, as the reaction proceeds, the nucleotides will be incorporated into the RNA molecule and consequently the total nucleotide concentration will be progressively reduced from its initial value.

In this context it is particularly preferred that the single nucleotides are provided in a concentration between 0.1 and 10 mM, preferably between 1 and 5 mM and most preferably in a concentration of 4 mM.

In case a 5' cap as defined below has to be generated at the 5'-end of the RNA, the in vitro transcription reaction mixture preferably further comprises a cap analog. In this context the concentration of GTP is preferably reduced compared to the other nucleotides (ATP, CTP and UTP). Preferably the cap analog is added with an initial concentration in the range of about 1 to 20 mM, 1 to 17.5 mM, 1 to 15 mM, 1 to 12.5 mM, 1 to 10 mM, 1 to 7.5 mM. Most preferably the cap analog is added in a concentration of 5.8 mM and the GTP concentration is reduced to a concentration of 1.45 mM whereas ATP, CTP and UTP are comprised in the reaction in a concentration of 4 mM each.

The ribonucleoside triphosphates (NTPs) GTP, ATP, CTP and UTP or analogs thereof may be provided with a monovalent or divalent cation as counterion. Preferably the monovalent cation is selected from the group consisting of $Li^+$, $Na^+$, $K^+$, $NH4^+$ or tris(hydroxymethyl)-aminomethane (Tris). Preferably, the divalent cation is selected from the group consisting of $Mg^{2+}$, $Ba^{2+}$ and $Mn^{2+}$.

As outlined in detail below, a part or all of at least one ribonucleoside triphosphate in the in vitro transcription reaction mixture may be replaced with a modified nucleoside triphosphate (as defined herein). In a preferred embodiment of the invention, said modified nucleoside triphosphate is selected from the group consisting of pseudouridine-5'-triphosphate, 1-methylpseudouridine-5'-triphosphate, 2-thiouridine-5'-triphosphate, 4-thiouridine-5'-triphosphate and 5-methylcytidine-5'-triphosphate. Other modified nucleotides which can be used in this context are listed below.

Following transcription, the DNA template can optionally be removed using methods known in the art comprising DNase I digestion. In this context, it is particularly preferred to add 6 µl DNAse I (1 mg/ml) and 0.2 µl $CaCl_2$ solution (0.1 M)/µg DNA template to the transcription reaction, and to incubate it for at least 3 h at 37° C.

Self-cleaving ribozyme (also referred to as "ribozyme"): A ribozyme is a catalytic RNA molecule capable of catalyzing reactions including site-specific cleavage of other nucleic acid molecules such as RNA molecules. The term ribozyme is used interchangeably with phrases such as catalytic RNA, enzymatic RNA, or RNA enzyme.

In the early 80s natural RNA molecules were discovered which are capable of catalyzing reactions in the absence of any protein component and these molecules were named ribozymes. Several classes of ribozymes occurring in natural systems have been discovered, most of which catalyse intramolecular splicing or cleavage reactions (reactions 'in cis'). The second possiblity are reactions 'in trans', wherein RNA enzymes cleave or modify target RNAs without becoming altered themselves.

In the present invention, in cis reactions are carried out by the encoded self-cleaving ribozyme.

Ribozymes are broadly grouped into two classes based on their size and reaction mechanisms: large and small ribozymes. The first group consists of the self-splicing group I and group II introns as well as the RNA component of RNase P, whereas the latter group includes the hammerhead, hairpin, hepatitis delta ribozymes and varkud satellite (VS) RNA as well as artificially selected nucleic acids. Large ribozymes consist of several hundred up to 3000 nucleotides and they generate reaction products with a free 3'-hydroxyl and 5'-phosphate group. In contrast, small catalytically active nucleic acids from 30 to ~150 nucleotides in length generate products with a 2'-3'-cyclic phosphate and a 5'-hydroxyl group (Schubert and Kurreck, 2004. Curr. Drug Targets 5(8):667-681). The second group is preferred herein.

Group I introns include the self-splicing intron in the pre-ribosomal RNA of the ciliate *Tetrahymena thermophilic*. Further examples of group I introns interrupt genes for rRNAs, tRNAs and mRNAs in a wide range of organelles and organisms. Group I introns perform a splicing reaction by a two-step transesterification mechanism: The reaction is initiated by a nucleophilic attack of the 3'-hydroxyl group of an exogenous guanosine cofactor on the 5'-splice site. Subsequently, the free 3'-hydroxyl of the upstream exon performs a second nucleophilic attack on the 3'-splice site to ligate both exons and release the intron. Substrate specificity of group I introns is achieved by an Internal Guide Sequence (IGS). The catalytically active site for the transesterification reaction resides in the intron.

Group II introns are found in bacteria and in organellar genes of eukaryotic cells. They catalyse a self-splicing reaction that is mechanistically distinct from group I introns because they do not require a guanosine cofactor. Instead, the 2'-hydroxyl of a specific adenosine at the so-called branch site of the intron initiates the reaction by a nucleophilic attack on the splice-site to form a lariat-type structure.

The hammerhead ribozyme is found in several plant virus satellite RNAs, viroids and transcripts of a nuclear satellite DNA of newt. This ribozyme is the smallest of the naturally occurring ribozymes and processes the linear concatamers that are generated during the rolling circle replication of circular RNA plant pathogens. The hammerhead ribozyme motif that has widely been applied since then comprises three helical sections connected via a three-way helical junction.

In hairpin ribozymes the catalytic entity is part of a four-helix junction. A minimal catalytic motif containing approximately 50 nucleotides has been identified that can be used for metal-ion dependent cleavage reactions in trans. It consists of two domains, each harbouring two helical regions separated by an internal loop, connected by a hinge region. One of these domains results from the association of 14 nucleotides of a substrate RNA with the ribozyme via base-pairing.

The hepatitis delta virus (HDV) ribozyme is found in a satellite virus of hepatitis B virus. Both the genomic and the antigenomic strand express cis-cleaving ribozymes of ~85 nucleotides that differ in sequence but fold into similar secondary structures. The crystal structure of the ribozyme reveals five helical regions are organized by two pseudoknot structures. The catalytic mechanism of the hepatitis delta virus ribozyme appears to involve the action of a cytosine base within the catalytic centre as a general acid-base catalyst. The hepatitis delta ribozyme displays high resistance to denaturing agents like urea or formamide.

The Varkud Satellite (VS) ribozyme is a 154 nucleotide long and is transcribed from a plasmid discovered in the mitochondria of certain strains of Neurospora. The VS ribozyme is the largest of the known nucleolytic ribozymes.

As noted above, an in cis reaction is carried out by the encoded self-cleaving ribozyme according to the present invention, wherein the cleavage site of this reaction lies close to its 5' end (in the meaning of +/−3, preferably +/−2, more preferably +/−1 nucleotide(s) from the exact 5' end of the sequence encoding the ribozyme) or exactly at its 5' end. It is noted that the encoded self-cleaving ribozyme according to the present invention fails to catalyze a self-circularization of the resulting RNA.

RNA polymerase terminator sequence element: This element comprises at least one discrete terminator sequence (also referred to as "termination sequence" or "terminator"), where the transcription by RNA polymerase terminates. Terminators cause release of the RNA and dissociation of the transcription complex. Two main types of termination sequences (Class 1 and Class 2) have been found to cause pausing or termination by RNA polymerase.

Class 1 termination sequences are thought to involve the formation of stem-loop structures in the nascent RNA transcripts. The typical class 1 terminator for bacteriophage RNA polymerase (such as T3, T7 and SP6 RNA polymerase) encodes an RNA sequence that can form a stable, GC-rich stem-loop followed by a string of U residues. Other examples of class 1 terminators include but are not limited to the T3-Tφ terminator and the termination signal identified in pBR322 at the end of the P4 transcription region (pBR322-P4 terminator; see, e.g., Lynakhov et al., J. Mol. Bio., 280, 201-213 (1998); Stuber D and Bujard H, Proc. Natl. Acad. Sci. USA, 78, 167-171 (1981)). A class 1 terminator domain is typically composed of a sequence located on the template strand of the DNA and consists of a region containing a sequence that is then repeated a few base pairs away in the inverted sequence (e.g., palindrome sequence). Typically the sequence is a G/C-rich stretch of nucleotides, followed by an A/T-rich stretch of nucleotides. It is assumed that the RNA molecule forms a short double-stranded region termed a hairpin or stem-loop. The hairpin slows down the RNA polymerase, causing it to pause in the A/T-rich region. The weak A-U base pairing in the DNA:RNA duplex allows the release of the complex, thereby terminating transcription (see, e.g., Enzymology Primer for Recombinant DNA Technology, ed. Hyone-Myong Eun, Academic Press, Inc., San Diego, (1996); Dunn J J and Studier F W, J. Mol. Bio., 166, 477-535 (1983)).

It appears that Class 2 terminator sequences do not encode RNAs with an apparently consistent secondary structure but these sequences rather seem to share a common DNA sequence. Typical class 2 terminator sequences are described in Lyakhov et al. (J. Mol. Biol. (1998) 280, 201-213), Macdonald et al. (J. Mol. Biol. (1993) 232, 1030-1047), Kwon and Kang (J. Biol. Chem. 1999, 274:29149-29155) and Du et al. (Biotechnology and Bioengineering, Vol. 109, No. 4, April, 2012).

In general, Class 2 terminator sequences are shorter than Class 1 terminator sequences and are thus preferred in the present method. In principle, any Class 2 terminator sequence or variant thereof may be used in the present invention. The following Class 2 terminator sequences are preferred in the context of the present invention:

| Name | Sequence (5' to 3') | SEQ ID No. |
|---|---|---|
| T7-CJ | TGTGTCCCTATCTGTTACAGTCTCCT | 12 |
| PTH | ATGCTTGCCATCTGTTTTCTTGCAAG | 13 |
| VSV | ATCCATGATATCTGTTAGTTTTTTTC | 14 |
| VSV-XhoI | ATCCATGATATCTGTTCTCGAGTTTTTTTC | 15 |
| rrnB T1 | TTTCGTTTTATCTGTTGTTTGTCGTG | 16 |
| Adeno5 | TAGTTTTGTATCTGTTTTGCAGCAGC | 17 |
| (λ P1) | TTCGAACCTCTCTGTTTACTGATAAG | 18 |
| T3-CJ | ATCTCTCTGTGTCCCTATCTGTTAGC | 19 |
| K11-CJ | ATGTCTCTGTGTCCCTATCTGTTGGT | 20 |
| rrnC | AAAATCATCCTTAGCGAAAGCTAAGGATTTTTTTATC | 21 |

Particularly preferred Class 2 terminator sequences are the VSV terminator sequence, the PTH terminator sequence, the rrnB T1 downstream terminator sequence, the rrnC terminator sequence and the concatemer junction sequence of the replicating T7 DNA (T7-CJ).

In the afore-mentioned publication by Kwon and Kang (J. Biol. Chem. 1999, 274:29149-29155), several variants of the rrnB T1 downstream terminator sequence were tested (referred to as "mutants of the rrnB t1 downstream termination signal", see in particular FIG. 3 of Kwon and Kang). The following Class 2 terminator sequences of these variants are also preferred in the context of the present invention:

| Name | Sequence | SEQ ID No. |
|---|---|---|
| 1W1 | TACCCCCTTTCGTTTTATCTGTTGTTTGTCGGTGAACG | 22 |
| 1W2 | TACCCCCTTTCGTTTTATCTGTTGTTTGTCGGGGCCCG | 23 |
| 1W3 | TACCCCCTTTCGTTTTATCTGTTGTTTGTCGTTTAAAG | 24 |
| 2W1 | TCGGGTACCCCGTTTTATCTGTTGTTTGTCGGTGAACG | 25 |
| 3W1 | CTCTAGAGTCCGTTTTATCTGTTGTTTGTCGGTGAACG | 26 |

-continued

| Name | Sequence | SEQ ID No. |
|---|---|---|
| 4W1 | CCTGCAGGTCCGTTTTATCTGTTGTTTGTCGGTGAACG | 27 |
| 2W7 | TCGGGTACCCGTTTTATCTGTTGTTTGTCGACCTGCA | 28 |
| 1I1 | TACCCCCTTTCGTTCCATCTGTTGTTTGTCGGTGAACG | 29 |
| 1I3 | TACCCCCTTTCGTTCCATCTGTTGTTTGTCGTTTAAAG | 30 |
| 1J1 | TACCCCCTTTCGTTCCATCTGTTCTTTCTCGGTGAACG | 31 |
| 5K1 | TCGGTACCCGCTTGCCATCTGTTGTTTGTCGGTGAACG | 32 |
| 1N1 | TACCCCCTTTCGTTTTATCTGTTCTTTCTCGGTGAACG | 33 |
| 1P10 | TACCCCCTTTCGTTCCATCTGTTTTCTTGCGACCTGCA | 34 |
| 5Q10 | TCGGTACCCGCTTGCCATCTGTTTTCTTGCGACCTGCA | 35 |
| 1R11 | TACCCCCTTTCGTTTTATCTGTTTTTTTTGGTGAACG | 36 |
| 1S11 | TACCCCCTTTCGTTCCATCTGTTTTTTTTGGTGAACG | 37 |
| 3Y8 | CTCTAGAGTCCGTTTTATCTGTTTGTTTGGACCTGCAGG | 38 |
| 4Y9 | CCTGCAGGTCCGTTTTATCTGTTTGTTTGGACTCTAGAG | 39 |
| 3Z8 | CTCTAGAGTCCGTTTTATCTGTTGTTTTGGACCTGCAGG | 40 |

A "variant" of a terminator sequence as mentioned herein is a sequence sharing a sequence identity below 100% with known terminator sequences, which is nevertheless still capable of acting as termination sequence for transcription. Potential variants can easily be tested by the skilled person for their activity as terminators, e.g. by the tests employed in Lyakhov et al. (J. Mol. Biol. (1998) 280, 201-213), or Kwon and Kang (J. Biol. Chem. 1999, 274:29149-29155), or as described in Example 1.

Purification of RNA: The inventive method comprises at least one step, preferably at least two steps, of purifying the RNA obtained by in vitro transcription in the respective step of the inventive method. In the following, exemplary purification steps are described, which may be used in preferred embodiments of the invention.

Alcoholic Precipitation: Sodium acetate and at least 95% ethanol are usually added to precipitate the RNA transcript. The reaction is then mixed and incubated at room temperature. Subsequently the reaction is centrifuged, the supernatant discarded and the RNA pellet washed with 75% ethanol. After drying, the RNA is preferably resuspended in water. This step also further ensures the removal of proteins from previous steps, if present. Moreover, the RNA-specific precipitation also removes contamination with residual plasmid DNA and bacterial (genomic) DNA, if present.

LiCl precipitation: High-molar LiCl solution is added to specifically precipitate the RNA transcript. LiCl precipitation is preferably performed by adding 50% of the volume 8M LiCl. The reaction is mixed and incubated at room temperature. Subsequently the reaction is centrifuged, the supernatant discarded and the RNA pellet washed with 75% ethanol. After drying, the RNA is preferably resuspended in water. This step also further ensures the removal of proteins from previous steps, if present. Moreover, the RNA-specific precipitation also removes contamination with residual plasmid DNA and bacterial (genomic) DNA, if present.

HPLC: HPLC (abbreviation for "High Performance (High Pressure) Liquid Chromatography") is an established method of separating mixtures of substances, which is widely used in biochemistry, analytical chemistry and clinical chemistry. An HPLC apparatus consists in the simplest case of a pump with eluent reservoir containing the mobile phase, a sample application system, a separation column containing the stationary phase, and the detector. In addition, a fraction collector may also be provided, with which the individual fractions may be separately collected after separation and are thus available for further applications.

Reversed phase HPLC consists of a non-polar stationary phase and a moderately polar mobile phase. The retention time is therefore longer for molecules, which are more non-polar in nature, allowing polar molecules to elute more readily. Retention time is increased by the addition of polar solvent to the mobile phase and decreased by the addition of more hydrophobic solvent.

The product RNA can be purified from various contaminations from previous manufacturing steps. These include buffer contaminations, protein impurities (*Escherichia coli* proteins, Restriction enzymes, T7-RNA-Polymerase, RNase-Inhibitor, DNase I, and BSA), impurities from RNA-RNA hybrids, from DNA-RNA hybrids or their fragments, from pDNA contaminations and bacterial genomic DNA contaminations, and solvent contaminations (Acetonitrile, Chloroform, TEAA, 2-Propanol and Phenol) and free nucleotides. Moreover, size exclusion occurs during that procedure (smaller and larger RNAs can be excluded).

Preferably, the reversed phase chromatography comprises using a porous reserved phase as stationary phase.

In a preferred embodiment of the method according to the invention, the porous reversed phase material is provided with a particle size of 8.0 µm to 50 µm, in particular 8.0 to 30 µm, still more preferably about 30 µm. The reversed phase material may be present in the form of small spheres. The method according to the invention may be performed particularly favorably with a porous reversed phase with this particle size, optionally in bead form, wherein particularly good separation results are obtained.

In another preferred embodiment, the reversed phase used in the method according to the invention may be porous and may have specific particle sizes. With stationary reversed phases which are not porous and thus differ completely with regard to particle size from the subject matter of the present invention as described for example by A. Azarani and K. H. Hecker (Nucleic Acids Research, vol. 29, no. 2 e7), on the other hand, excessively high pressures are built up, such that preparative purification of the RNA is possible only with great difficulty, if at all.

In a preferred embodiment of the method according to the invention, the reversed phase has a pore size of 1000 Å to 5000 Å, in particular a pore size of 1000 Å to 4000 Å, more preferably 1500 Å to 4000 Å, 2000 Å to 4000 Å or 2500 Å to 4000 Å. Particularly preferred pore sizes for the reversed phases are 1000 Å to 2000 Å, more preferably 1000 Å to 1500 Å and most preferably 1000 Å to 1200 Å or 3500-4500 Å. Most preferred is a pore size of 4000 Å. With a reversed phase having these pore sizes, particularly good results are achieved with regard to purification of the RNA using the method according to the invention, in particular the elevated pressures built up in the method according to A. Azarani and K. H. Hecker are thus avoided, whereby preparative separation is made possible in a particularly favourable manner. At pore sizes of below 1000 Å separation of RNA molecules becomes poorer.

A pore size of 1000 Å to 5000 Å, in particular a pore size of 1000 Å to 4000 Å, more preferably 1500 Å to 4000 Å, 2000 Å to 4000 Å or 2500 Å to 4000 Å may be suitable to separate a RNA from other components of a mixture, the RNA having a size as mentioned above of up to about 15000 nucleotides (as single stranded RNA molecule) or base pairs (as double stranded RNA molecule), in particular 100 to 10000, more preferably 500 to 10000 nucleotides or base pairs, even more preferably 800 to 5000 nucleotides or base pairs and even more preferably 800 to 2000 nucleotides or base pairs. However, the pore size of the reversed phase may also be selected in dependence of the size of the RNA to be separated, i.e. a larger pore size may be selected, if larger RNA molecules are to be separated and smaller pore sizes may be selected, if smaller RNA molecules may be selected. This is due to the effect that the retention of the RNA molecules and the separation not only depends on the interaction of the (reversed) phase but also on the possibility of molecules to get inside the pores of the matrix and thus provide a further retention effect. Without being limited thereto, e.g. a pore size for the reversed phase of about 2000 Å to about 5000 Å, more preferably of about 2500 to about 4000, most preferably of about 3500 to about 4500 Å, may thus be used to separate larger RNA molecules, e.g. RNA molecules of 100 to 10000, more preferably 500 to 10000 nucleotides or base pairs, even more preferably 800 to 5000 nucleotides or base pairs and even more preferably 800 to 2000 nucleotides or base pairs. Alternatively, without being limited thereto, a pore size for the reversed phases of about 1000 Å to about 2500 Å, more preferably of about 1000 Å to about 2000 Å, and most preferably of about 1000 Å to 1200 Å may be used to separate smaller RNA molecules, e.g. RNA molecules of about 30-1000, 50-1000 or 100-1000 or 20-200, 20-100, 20-50 or 20-30 nucleotides may also be separated in this way.

In general, any material known to be used as reverse phase stationary phase, in particular any polymeric material may be used for the inventive method, if that material can be provided in porous form. The stationary phase may be composed of organic and/or inorganic material. Examples for polymers to be used for the present invention are (non-alkylated) polystyrenes, (non-alkylated) polystyrenedivinylbenzenes, silica gel, silica gel modified with non-polar residues, particularly silica gel modified with alkyl containing residues, more preferably with butyl-, octyl and/or octadecyl containing residues, silica gel modified with phenylic residues, polymethacrylates, etc. or other materials suitable e.g. for gel chromatography or other chromatographic methods as mentioned above, such as dextran, including e.g. Sephadex® and Sephacryl® materials, agarose, dextran/agarose mixtures, polyacrylamide, etc.

In a particularly preferred embodiment, the material for the reversed phase is a porous polystyrene polymer, a (non-alkylated) (porous) polystyrenedivinylbenzene polymer, porous silica gel, porous silica gel modified with non-polar residues, particularly porous silica gel modified with alkyl containing residues, more preferably with butyl-, octyl and/or octadecyl containing residues, porous silica gel modified with phenylic residues, porous polymethacrylates, wherein in particular a porous polystyrene polymer or a non-alkylated (porous) polystyrenedivinylbenzene may be used. Stationary phases with polystyrenedivinylbenzene are known per se. The per se known polystyrenedivinyl-benzenes already used for HPLC methods, which are commercially obtainable, may be used for the method according to the invention.

A non-alkylated porous polystyrenedivinylbenzene which is very particularly preferred for the method according to the invention is one which, without being limited thereto, may have in particular a particle size of 8.0±1.5 μm, in particular 8.0±0.5 μm, and a pore size of 1000-1500 Å, in particular 1000-1200 Å or 3500-4500 Å and most preferably a particle size of 4000 Å. With this material for the reversed phases, the above-described advantages of the method according to the invention may be achieved in a particularly favorable manner.

This stationary phase described in greater detail above is conventionally located in a column. V2A steel is conventionally used as the material for the column, but other materials may also be used for the column provided they are suitable for the conditions prevailing during HPLC. Conventionally the column is straight. It is favorable for the HPLC column to have a length of 5 cm to 100 cm and a diameter of 4 mm to 50 cm. Columns used for the method according to the invention may in particular have the following dimensions: 25 cm long and 20 mm in diameter or 25 cm long and 50 mm in diameter, or 25 cm long and 10 cm in diameter or any other dimension with regard to length and diameter, which is suitable for preparative recovery of RNA, even lengths of several metres and also larger diameters being feasible in the case of upscaling. The dimensions are here geared towards what is technically possible with liquid chromatography.

Selection of the mobile phase depends on the type of separation desired. This means that the mobile phase established for a specific separation, as may be known for example from the prior art, cannot be straightforwardly applied to a different separation problem with a sufficient prospect of success. For each separation problem, the ideal elution conditions, in particular the mobile phase used, have to be determined by empirical testing.

In a preferred embodiment of the HPLC method according to the invention, a mixture of an aqueous solvent and an organic solvent is used as the mobile phase for eluting the RNA. It is favorable for a buffer to be used as the aqueous solvent which has in particular a pH of 6.0-8.0, for example of about 7, for example. 7.0; preferably the buffer is triethylammonium acetate (TEAA), particularly preferably a 0.02 M to 0.5 M, in particular 0.08 M to 0.12 M, very particularly an about 0.1 M TEAA buffer, which, as described above, also acts as a counterion to the RNA in the ion pair method.

In a preferred embodiment, the organic solvent which is used in the mobile phase comprises acetonitrile, methanol, ethanol, 1-propanol, 2-propanol and acetone or a mixture thereof, very particularly preferably acetonitrile. With these organic solvents, in particular acetonitrile, purification of the RNA proceeds in a particularly favourable manner with the method according to the invention.

In a particularly preferred embodiment of the method according to the invention, the mobile phase is a mixture of 0.1 M triethylammonium acetate, pH 7, and acetonitrile.

It has proven particularly favorable for the method according to the invention for the mobile phase to contain 5.0 vol. % to 25.0 vol. % organic solvent, relative to the mobile phase, and for this to be made up to 100 vol. % with the aqueous solvent. Typically, in the event of gradient separation, the proportion of organic solvent is increased, in particular by at least 10%, more preferably by at least 50% and most preferably by at least 100%, optionally by at least 200%, relative to the initial vol. % in the mobile phase. In a preferred embodiment, in the method according to the invention the proportion of organic solvent in the mobile phase amounts in the course of HPLC separation to 3 to 9, preferably 4 to 7.5, in particular 5.0 vol. %, in each case relative to the mobile phase. More preferably, the proportion of organic solvent in the mobile phase is increased in the course of HPLC separation from 3 to 9, in particular 5.0 vol.

% to up to 20.0 vol. %, in each case relative to the mobile phase. Still more preferably, the method is performed in such a way that the proportion of organic solvent in the mobile phase is increased in the course of HPLC separation from 6.5 to 8.5, in particular 7.5 vol. %, to up to 17.5 vol. %, in each case relative to the mobile phase.

It has proven even more particularly favorable for the method according to the invention for the mobile phase to contain 7.5 vol. % to 17.5 vol. % organic solvent, relative to the mobile phase, and for this to be made up to 100 vol. % with the aqueous buffered solvent.

In the case of the method according to the invention elution may proceed isocratically or by means of gradient separation. In isocratic separation, elution of the RNA proceeds with a single eluent or a constant mixture of a plurality of eluents, wherein the solvents described above in detail may be used as eluent.

In a preferred embodiment of the method according to the invention, gradient separation is performed. In this respect, the composition of the eluent is varied by means of a gradient program. The equipment necessary for gradient separation is known to a person skilled in the art. Gradient elution may here proceed either on the low pressure side by mixing chambers or on the high pressure side by further pumps.

Preferably, in the method according to the invention, the proportion of organic solvent, as described above, is increased relative to the aqueous solvent during gradient separation. The above-described agents may here be used as the aqueous solvent and the likewise above-described agents may be used as the organic solvent.

For example, the proportion of organic solvent in the mobile phase may be increased in the course of HPLC separation from 5.0 vol. % to 20.0 vol. %, in each case relative to the mobile phase. In particular, the proportion of organic solvent in the mobile phase may be increased in the course of HPLC separation from 7.5 vol. % to 17.5 vol. %, in particular 9.5 to 14.5 vol. %, in each case relative to the mobile phase.

The flow rate of the eluent is so selected that good separation of the RNA from the other constituents contained in the sample to be investigated takes place. The eluent flow rate selected for the method according to the invention may amount to from 1 ml/min to several litres per minute (in the case of upscaling), in particular about 1 to 1000 ml/min, more preferably 5 ml to 500 ml/min, even more preferably more than 100 ml/min, depending on the type and scope of the upscaling. This flow rate may be established and regulated by the pump.

Detection proceeds favorably with a UV detector at 254 nm, wherein a reference measurement may be made at 600 nm. However, any other detection method may alternatively be used, with which the RNA described above in greater detail may be detected in satisfactory and reliable manner.

In preferred embodiments, the RP-HPLC is performed as described in WO 2008/077592.

Anion exchange chromatography (AEX): AEX chromatography is an alternative method of purification that leverages ionic interaction between positively charged sorbents and negatively charged molecules. AEX sorbents typically include a charged functional group cross-linked to solid phase media. Ion exchange chromatography for preparative RNA transcript also provides a solution that allows for separations of longer RNA transcripts, including lengths of up to at least 10,000 nucleotides. In addition, the methods allow for separations of chemically modified RNA transcripts (see also WO2014144767A1).

A sample comprising the RNA transcript is preferably contacted with an ion exchange sorbent comprising a positively-charged functional group linked to solid phase media, and the sample is delivered with at least one mobile phase, where the RNA transcript in the sample binds the positively-charged functional group of the ion exchange sorbent. In one embodiment, the sample is delivered under denaturing conditions, for example, the sample can be contacted with urea. In other embodiments, the mobile phase is a Tris-EDTA-acetonitrile buffered mobile phase, or there are two mobile phases made of Tris-EDTA-acetonitrile. In other embodiments, the mobile phase comprises a chaotropic salt, such as sodium perchlorate. The ion exchange sorbent elutes a portion of the sample comprising the RNA transcript and one or more separate portions of the sample comprising any impurities. At least one aspect of the portion of the sample comprising the RNA transcript and the separate portions of the sample comprising the impurities are then analyzed, where the aspect is charge heterogeneity of the RNA transcript, mass heterogeneity of the RNA transcript, process intermediates, impurities, or degradation products. The RNA transcript is then characterized by using the analysis to determine the charge heterogeneity of the RNA transcript.

Affinity chromatography (oligo-dT): In one embodiment, the poly A capture based affinity purification is oligo dT purification. For example, a polythymidine ligand is immobilized to a derivatized chromatography resin. The mechanism of purification involves hybridization of the poly A tail of the RNA transcript to the oligonucleotide ligand. The DNA template will not bind. In addition, RNA transcripts that do not contain Poly A stretches (short aborts and other truncates formed during in vitro transcription) will not bind to the resin and will not form a duplex with the affinity ligand. Poly adenylated RNA can then be eluted from the resin utilizing a low ionic strength buffer or a competitive binding oligonucleotide solution. A one pot purification method can yield highly purified poly A containing RNA with recoveries >80% actively removes endotoxin, DNA template, and enzymes utilized in the production of RNA using a simple capture and elute methodology with no subsequent fraction of captured poly A containing RNA. This purification increases mRNA product purity and in turn significantly increases target protein expression.

Hydroxyapatite chromatography: Purification of RNA transcript is described in WO2014140211. Hydroxyapatite chromatography involves hydroxyapatite as stationary phase. Hydroxyapatite is a form of calcium phosphate having the chemical formula $Ca_5(PO_4)_3(OH)$. Hydroxyapatite chromatography of nucleic acids is believed to exploit the charge interaction between their negatively charged phosphate backbone and the positively charged calcium ions on the surface of the hydroxyapatite medium. Differential elution (e.g. to separate protein, DNA and undesired RNA species from desired RNA species) is accomplished by the application of an increasing phosphate gradient. Phosphate ions present in the buffer compete with the phosphate groups of the retained nucleic acid species for calcium on the hydroxyapatite medium, thus allowing separation by selective elution of molecules. In this mixed mode chromatography, the binding is a balance of attraction of the RNA phosphate backbone to the calcium ions of the hydroxyapatite medium and repulsion of the RNA phosphate backbone from the phosphate of the hydroxyapatite medium. Compared to ion exchange chromatography, the strength of the binding on a hydroxyapatite medium is dependent on charge density rather than total charge. This important difference allows for the separation of molecules upon their charge density (e.g. RNA vs DNA vs proteins) and the binding and elution of RNA regardless of its total charge, and therefore regardless of its length. Therefore this method can be used for the purification of RNA molecules of any length. The fractionation of nucleic acids using hydroxyapatite was described in the 1960s (Bernardi et al. 1965). This approach has been exploited for applications including isolation and separation of viral RNA, dsDNA and ssDNA from environmental samples (Andrews-Pfannkoch et al. 2010), separation of DNA and RNA from tissue-extracted nucleic acids (Beland et al. 1979) and separation of DNA for hybridization studies (Kamalay et al. 1984).

Core bead chromatography: Purification of RNA transcript by core bead chromatography is described in WO 2014140211A1 and does not require prior DNA digest. Preferably, RNA is selectively recovered from the column in the flow-through. Proteins and short nucleic acids are retained in the beads. Flow-through fractions containing RNA may be identified by measuring UV absorption at 260 nm. The composition comprising the RNA of interest collected in the flow-through is highly purified relative to the preparation before the core bead chromatography step. Multiple eluted fractions containing the RNA of interest may be combined before further treatment. An exemplary core bead flow-through chromatography medium is Capto™ Core 700 beads from GE Healthcare. Suitable chromatography setups are known in the art, for example liquid chromatography systems such as the AKTA liquid chromatography systems from GE Healthcare.

Parameters can be set in a way that pDNA and proteins are captured in the beads, and RNA products flow through. Afterwards, HPLC purification can be conducted to get rid of RNA fragments etc.

Alternatively or additionally the RNA is recovered by other purification methods (e.g. affinity chromatography, size exclusion chromatography, anion exchange chromatography, etc.)

Tangential Flow Filtration (TFF) or Crossflow Filtration: TFF is different from dead-end filtration, in which the feed is passed through a membrane or bed, the solids being trapped in the filter and the filtrate being released at the other end. Cross-flow filtration is called this way because the majority of the feed flow travels tangentially across the surface of the filter, rather than into the filter. The principal advantage of this is that the filter cake (which can blind the filter) is substantially washed away during the filtration process, increasing the length of time that a filter unit can be operational. It can be a continuous process, contrary to batch-wise dead-end filtration. This type of filtration is typically selected for feeds containing a high proportion of small particle size solids (where the permeate is of most value) because solid material can quickly block (blind) the filter surface with dead-end filtration. Applied pressure causes one portion of the flow stream to pass through the membrane (filtrate/permeate) while the remainder (retentate) is recirculated back to the feed reservoir. The general working principle of TFF can be found in literature, see e.g. Fernandez et al. (A BIOTECHNOLOGICA, Bd. 12, 1992, Berlin, Pages 49-56) or Rathore, A S et al (Prep Biochem Biotechnol. 2011; 41(4):398-421). The primary applications for TFF are concentration, diafiltration (desalting and buffer/solvent exchange), and fractionation of large from small biomolecules. Membranes with different molecular weight cutoffs (MWCO) may be used for TFF. In the context of the present invention, ultrafiltration membranes can preferably be used for TFF. Two basic filter configurations are generally used for TFF. In cartridge filters (often called hollow fiber filters), the membrane forms a set of parallel hollow fibers. The feed stream passes through the lumen of the fibers and the permeate is collected from outside the fibers. Cartridges are characterized in terms of fiber length, lumen diameter and number of fibers, as well as filter pore size. In cassette filters, several flat sheets of membrane are held apart from each other and from the cassette housing by support screens. The feed stream passes into the space between two sheets and permeate is collected from the opposite side of the sheets. Cassettes are characterized in terms of flow path length and channel height, as well as membrane pore size. The channel height is determined by the thickness of the support screen. Both cartridges and cassettes are constructed from materials chosen for mechanical strength, chemical and physical compatibility, and low levels of extractable and/or toxic compounds.

Linearizing circular DNA: Linear DNA is obtained by contacting circular DNA with a restriction enzyme under suitable conditions so that the restriction enzyme cuts the circular DNA at its recognition site(s) and disrupts the circular DNA structure. Hence, linear template DNA comprises a free 5' end and a free 3' end, which are not linked to each other.

Restriction enzymes: Restriction enzymes are a class of enzymes that occur naturally in bacteria and in some viruses. Restriction enzymes can be used in the laboratory e.g. to cleave DNA molecules into smaller fragments for molecular cloning and gene characterization. A restriction enzyme is an enzyme that cuts DNA at or near specific recognition nucleotide sequences known as restriction sites. Restriction enzymes are commonly classified into four types, which differ in their structure and whether they cut their DNA substrate at their recognition site, or if the recognition and cleavage sites are separate from one another. To cut DNA, all restriction enzymes make two incisions, one per each sugar-phosphate backbone (i.e. each strand) of the DNA double helix.

Restriction site: A restriction site, also called restriction enzyme recognition site, is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence. Most restriction endonucleases recognize palindromic or partially palindromic sites. A palindrome is defined as dyad symmetry around an axis. For example, EcoRI digestion produces "sticky" ends, whereas SmaI restriction enzyme cleavage produces "blunt" ends. Recognition sequences in DNA differ for each restriction enzyme, producing differences in the length, sequence and strand orientation (5' end or the 3' end) of a sticky-end "overhang" of an enzyme restriction. Different restriction enzymes that recognize the same sequence are known as neoschizomers. These often cleave in different locales of the sequence. Different enzymes that recognize and cleave in the same location are known as isoschizomers.

Modified nucleoside triphosphate: The term "modified nucleoside triphosphate" as used herein refers to chemical modifications comprising backbone modifications as well as sugar modifications or base modifications. These modified nucleoside triphosphates are also termed herein as (nucleotide) analogs, modified nucleosides/nucleotides or nucleotide/nucleoside modifications.

In this context, the modified nucleoside triphosphates as defined herein are nucleotide analogs/modifications, e.g. backbone modifications, sugar modifications or base modifications. A backbone modification in connection with the present invention is a modification, in which phosphates of the backbone of the nucleotides are chemically modified. A sugar modification in connection with the present invention is a chemical modification of the sugar of the nucleotides. Furthermore, a base modification in connection with the present invention is a chemical modification of the base moiety of the nucleotides. In this context nucleotide analogs or modifications are preferably selected from nucleotide analogs which are applicable for transcription and/or translation.

Sugar modifications: The modified nucleosides and nucleotides, which may be used in the context of the present invention, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), -0(CH2CH2o)nCH2CH2OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleotide can include nucleotides containing, for instance, arabinose as the sugar.

Backbone Modifications: The phosphate backbone may further be modified in the modified nucleosides and nucleotides. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications: The modified nucleosides and nucleotides, which may be used in the present invention, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogs/modifications are selected from base modifications, which are preferably selected from 2-amino-6-chloropurineriboside-5'-triphosphate, 2-Aminopurine-riboside-5'-triphosphate; 2-amino adenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyluridine, 1-carboxymethyl-pseudouridine, 5-propynyluridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8- aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments the modified nucleotides include nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Further modified nucleotides have been described previously (see, e.g., WO 2013/052523).

5'-cap: A 5'-cap is an entity, typically a modified nucleotide entity, which generally "caps" the 5'-end of a mature mRNA and increases its stability. A 5'-cap may typically be formed by a modified nucleotide (cap analog), particularly by a derivative of a guanine nucleotide. Preferably, the 5'-cap is linked to the 5'-terminus of the RNA via a 5'-5'-triphosphate linkage. A 5'-cap may be methylated, e.g. m7GpppN (e.g. m7G(5')ppp(5')G (m7G)), wherein N is the terminal 5' nucleotide of the nucleic acid carrying the 5'-cap, typically the 5'-end of an RNA, m7 is a methyl group attached to position 7 of the guanine (G) and ppp is the triphosphate. Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methyl-phosphonate moiety. Further modified 5'-CAP structures which may be used in the context of the present invention are CAP1 (methylation of the ribose of the adjacent nucleotide of m7GpppN), CAP2 (methylation of the ribose of the 2nd nucleotide downstream of the m7GpppN), CAP3 (methylation of the ribose of the 3rd nucleotide downstream of the m7GpppN), CAP4 (methylation of the ribose of the 4th nucleotide downstream of the m7GpppN), ARCA (anti-reverse CAP analogue), modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Rolling circle amplification (RCA): RCA uses a circular DNA as template and random hexamer primers that anneal to the circular template DNA at multiple sites. No sequence-specific primers are thus required. Usually, Phi29 DNA polymerase is used to extend each of the primers. The reaction is performed at 30° C. and thus without the need for thermocycling (i.e. the use of different temperatures for different steps). When the DNA polymerase reaches a downstream-extended primer, strand displacement synthesis occurs and the displaced strand is rendered single-stranded and available to be primed by more hexameric primers. This process continues and results in exponential, isothermal amplification. FIG. 9 shows a scheme of RCA. Usually, RCA is used in DNA sequencing. RCA is described e.g. in Dean et al. (Genome Res. 2001 June; 11(6):1095-9) and Kumar and Chernaya (Biotechniques. 2009 July; 47(1):637-9. doi: 10.2144/000113171).

Plasmid DNA: The term "plasmid DNA" refers to a circular nucleic acid molecule, preferably to an artificial nucleic acid molecule. Such plasmid DNA constructs may be storage vectors, expression vectors, cloning vectors, transfer vectors etc. Preferably, a plasmid DNA within the meaning of the present invention comprises in addition to the elements described herein a multiple cloning site, optionally a selection marker, such as an antibiotic resistance factor, and a sequence suitable for multiplication of the vector, such as an origin of replication. Typical plasmid backbones are e.g. pUC19 and pBR322.

Linker sequence (also referred to as "linker"): A linker is typically a short nucleotide sequence which links two functional domains, but does not have a biological function itself. Linkers that can be used in the present invention may comprise between 1 and 30 nucleotides, preferably between 3 and 25 nucleotides, more preferably between 5 and 20 nucleotides and most preferably between 8 and 16 nucleotides. A linker may comprise about 5, about 6, about 7, about 8, about 9, about 10, about 11, about 12, about 13, about 14, about 15, or about 16 nucleotides.

DETAILED DESCRIPTION OF THE FINDINGS UNDERLYING THE PRESENT INVENTION

The inventors of the present application surprisingly found that a method as disclosed herein can be applied to produce a target RNA to a desired yield and in a desired quality. This in particular refers to a situation, where the method of the present invention is compared to a method using linearized DNA as DNA template (opposite to the use of circular DNA as DNA template in the present method), and the comparison shows that at least an identical yield and at least an identical quality (mainly in terms of integrity of the length of the RNA) of the target RNA is obtained by a method disclosed herein. It was found by the inventors that the self-cleaving ribozyme sequence and any sequences 3' thereof can efficiently be separated from the target RNA by a purification step. An advantage over the comparative method using linearized DNA resides therein that the step of linearizing a circular DNA is not required in the method disclosed herein. This will save time for the production of the target RNA and will result in a more cost-efficient method of production since the step of linearization using expensive restriction enzymes and purification steps of the linearized template DNA can be omitted.

Thus, the method disclosed herein can in particular be used to produce a target RNA, wherein the method is time- and cost-efficient, scalable and provides RNA at high purity.

It was then further surprisingly found that the method can also be applied using modified nucleotides. It is to be emphasized that this result was obtained using all ratios tested herein, wherein in one of the tests even 100% of Pseudo-UPT (pseudouridine-5'-triphosphate) and 100% of 5-methyl CTP (5-methylcytidine-5'-triphosphate) were used. This was rather unexpected in view of the potential negative influence of modified nucleotides on the termination efficacy and/or the efficacy of the self-cleaving ribozyme.

Thus, the method disclosed herein can in particular be used to produce a target RNA comprising modified nucleotides, wherein the method is time- and cost-efficient, scalable and provides RNA at high purity.

As noted above, yield and quality of the RNA produced by the present method are in particular determined by comparison to a method using linear DNA template (and not circular DNA template as in the present method). Two surprising findings were made in the present invention:
1) The method disclosed herein provides the desired yield and quality of the target RNA if the method is carried out with a low concentration or amount of template DNA that is provided in step a) [e.g. in a concentration range of about 0.0005 g/L to about 0.002 g/L; preferably in a concentration of about 0.001 g/L], which is then amplified by rolling circle amplification (RCA) in order to obtain multimeric DNA, wherein said multimeric DNA obtained by RCA of said circular DNA is then used as template DNA in the concentration, at which linear DNA is used [e.g. in a concentration range of about 0.02 g/L to about 0.1 g/L, preferably in a concentration of about 0.05 g/L] for the in vitro transcription in step b). Thus, there is no need for traditional amplification methods using i) fermentative proliferation in and subsequent isolation from bacteria or ii) PCR methods using specific primers and thermocycling.
2) The method disclosed herein provides the desired yield and quality of the target RNA if the method is carried out i) without any amplification step but ii) with a higher concentration of the circular DNA provided in step a) compared to the concentration of linear DNA in a corresponding method using linear DNA. Preferably, the ratio of [concentration of circular DNA provided in step a) as DNA template] to [concentration of linear DNA template in a corresponding assay] is from about 5:1 to 1.5:1, preferably from 4:1 to 2:1, most preferably 3:1. The concentration range of the circular DNA may be in the range of about 0.075 g/L to about 0.3 g/L, preferably from about 0.1 g/L to about 0.2 g/L. Particularly preferred is a concentration of about 0.15 g/L. For comparative reasons it is noted that, as also stated in a standard in vitro transcription reaction defined above, the concentration of linear DNA as template DNA in a standard method is about 0.05 g/L.

Finally, it was surprisingly found that the method disclosed herein can be used to produce mRNA, wherein said mRNA provides at least the expression capability of mRNA produced by a method not resulting in a 2'3' cyclic phosphate at the 3' end of the mRNA (e.g. a method relying on in vitro transcription using linearized DNA). This finding is of particular relevance if the further use of the produced mRNAs is considered, namely the production of the encoded protein by translation in vitro or in vivo.

Further preferred embodiments:
1. A method of producing a target RNA comprising the steps of:
    a) providing a circular DNA as template DNA comprising the following sequence elements from 5' to 3':
        i. an RNA polymerase promoter sequence operably linked to
        ii. a sequence encoding said target RNA operably linked to
        iii. a sequence encoding a self-cleaving ribozyme, wherein said self-cleaving ribozyme cleaves close to or at its 5' end, operably linked to
        iv. an RNA polymerase terminator sequence element; and
    b) in vitro transcription of said template DNA to obtain said target RNA;
    c) purifying said target RNA by at least one purification step in order to obtain purified target RNA;
wherein said method does not comprise a step of linearizing said circular DNA provided in step a).
2. The method according to embodiment 1, wherein the in vitro transcription in step b) is carried out in the presence of naturally occurring nucleotides and at least one modified nucleotide, wherein said at least one modified nucleotide at least partially replaces at least one naturally occurring nucleotide.
3. The method according to embodiment 1 or 2, wherein the in vitro transcription in step b) is carried out in the presence of a cap analog.
4. The method according to any one of embodiments 1 to 3, wherein said target RNA is purified in step c) by at least one first and at least one second purification step.
5. The method according to embodiment 4, wherein the at least one first purification step comprises a precipitation step and the at least one second purification step comprises a chromatographic step.
6. The method according to embodiment 5, wherein the at least one first purification step comprises an alcohol precipitation step or a LiCl precipitation step and the at least one second purification step comprises a chromatographic step selected from the group consisting of HPLC, anion exchange chromatography, affinity chromatography, hydroxyapatite chromatography and core bead chromatography.
7. The method according to embodiment 4, wherein the at least one first purification step comprises a tangential flow filtration step and the at least one second purification step comprises a chromatographic step.
8. The method according to embodiment 7, wherein the at least one first purification step comprises a diafiltration step using tangential flow filtration and/or a concentration step using tangential flow filtration and the at least one second purification step comprises a chromatographic step selected from the group consisting of HPLC, anion exchange chromatography, affinity chromatography, hydroxyapatite chromatography and core bead chromatography.
9. The method according to any one of the preceding embodiments, wherein said circular DNA provided in step a) is amplified by rolling circle amplification prior to the in vitro transcription in step b).

10. The method according to any one of embodiments 1 to 8, wherein said method does not comprise a step of amplifying said circular DNA and said circular DNA is provided in step a) at a concentration ranging from about 0.075 g/L to about 0.3 g/L, preferably from about 0.1 g/L to about 0.2 g/L.

11. A circular DNA comprising the following sequence elements from 5' to 3':
   a) an RNA polymerase promoter sequence operably linked to
   b) a sequence encoding a target RNA operably linked to
   c) a sequence encoding a self-cleaving ribozyme, wherein said self-cleaving ribozyme cleaves close to or at its 5' end, operably linked to
   d) an RNA polymerase terminator sequence element.

12. The circular DNA according to embodiment 11, wherein said RNA polymerase promoter sequence is a T7 RNA polymerase promoter sequence.

13. The circular DNA according to embodiment 11 or 12, wherein said target RNA is selected from the group consisting of mRNA, viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

14. The circular DNA according to any one of embodiments 11 to 13, wherein said self-cleaving ribozyme encoded in sequence element c) is selected from the group consisting of a hepatitis delta virus (HDV) ribozyme, a hammerhead ribozyme and a hairpin ribozyme.

15. The circular DNA according to any one of embodiments 11 to 14, wherein said RNA polymerase terminator sequence element comprises at least one Class II termination sequence and fails to comprise a Class I termination sequence.

16. The circular DNA according to any one of embodiments 11 to 15, wherein said RNA polymerase terminator sequence element comprises at least two Class II termination sequences, wherein said at least two Class II termination sequences are optionally separated by a spacer sequence.

17. The circular DNA according to any one of embodiments 11 to 16, wherein said RNA polymerase terminator sequence element comprises at least three Class II termination sequences, wherein said at least three Class II termination sequences are optionally separated by a spacer sequence.

18. The circular DNA according to any one of embodiments 11 to 17, wherein said RNA polymerase terminator sequence element comprises at least four Class II termination sequences, wherein said at least four Class II termination sequences are optionally separated by a spacer sequence.

19. The circular DNA according to any one of embodiments 16 to 18, wherein said Class II termination sequences are independently selected from the group consisting of the VSV terminator sequence, the PTH terminator sequence, the rrnB T1 downstream terminator sequence, the rrnC terminator sequence, the concatemer junction sequence of the replicating T7 DNA, and a variant of any of the foregoing.

20. The circular DNA according to any one of embodiments 16 to 19, wherein said Class II termination sequences are identical.

21. The circular DNA according to embodiment 20, wherein said Class II termination sequences are VSV terminator sequences or 1R11 variant rrnB T1 downstream terminator sequences.

22. A multimeric DNA obtained by rolling circle amplification of said circular DNA according to any one of embodiments 11 to 21.

23. Use of a circular DNA according to any one of embodiments 11 to 21 or a multimeric DNA according to embodiment 22 in a method according to any one of embodiments 1 to 10.

24. Use of a method according to any one of embodiments 1 to 10 to produce mRNA as target RNA, wherein said mRNA provides at least the expression capability of mRNA produced by a method not resulting in a 2'3' cyclic phosphate at the 3' end of the mRNA.

EXAMPLES

The following Examples are merely illustrative and shall describe the present invention in a further way. These Examples shall not be construed to limit the present invention thereto.

Example 1

Materials and Methods Used Herein

Cloning, amplification and purification of plasmids used herein: The starting plasmid used for the production of plasmids used herein contained a T7 promoter sequence followed by a sequence coding for the target RNA and single restriction sites for EcoRI, XbaI and NdeI (in this order). One SspI restriction site was present in the vector backbone 119 nts upstream of the T7 promoter sequence. A terminator sequence element (for p1, see Table 1 below) and a ribozyme-terminator sequence element (for p2 and p3, see Table 1 below) were synthesized (Geneart, Life Technologies) with several nucleotides added at the 5' and 3'-ends for efficient restriction hydrolysis. The terminator sequence element for p1 was cloned via the XbaI and NdeI restriction sites by standard restriction-ligation cloning into the starting plasmid (see Green and Sambrook: Molecular Cloning: A Laboratory Manual; enzymes were bought from Thermo scientific). The ribozyme-terminator sequence elements for p2 and p3 were cloned via the EcoRI and NdeI restriction sites also by standard restriction-ligation cloning. A further plasmid (p3-mod) was prepared by exchanging the ribozyme in p3 for a variant with the ribozyme-sequence given in Table 1 below for p3-mod, wherein this variant was cloned into EcoRI I XbaI linearized and gel-purified p2 using the Gibson assembly kit (from NEB) and the fragment with SEQ ID No. 11 (Geneart, Life Technologies) according to the manufacturer's recommendations. After cloning, the plasmids were amplified in E. coli DH5α competent cells (from Life Technologies) and purified from cultures thereof with the Nucleobond Xtra Maxi EF kit (Macherey-Nagel) according to the manufacturer's recommendations.

TABLE 1

Sequence motifs used to generate p1 (SEQ ID No: 1), p2 (SEQ ID No: 2), p3 (SEQ ID No: 3) and p3-mod (SEQ ID No: 4) as DNA templates for the in vitro transcription of RNA. The size of the plasmids is given together with the expected size of the target RNA and with the expected size of the large read-through fragment from SspI linearized templates. Note that this large read-through fragment is not cut in p1 due to the absence of a ribozyme (and thus also comprises the target RNA). In p2 and p3, due to the presence of the ribozyme, there are basically two products in p2 and p3 after ribozyme cleavage: the target RNA and a second fragment comprising at the 5' end the ribozyme and running to the SspI site. Restriction sites are given in italics and underlined sequences indicate terminator sequences.

| Plasmid | Total size (bp) | Ribozyme sequence | Terminator sequence element | Size of target RNA (nts) | Large read-through fragment (nts) |
|---|---|---|---|---|---|
| p1 | 3941 | None | 1xVSV terminator (SEQ ID No: 5): *TCTAGA*ATCCATG*ATATCT*GTTA GTTTTTTTCTACTAGAG*CATATG* | 1900 | 3808 |
| p2 | 4038 | SEQ ID No: 8 (identical to p3) | 2x1R11 terminator, no spacer (SEQ ID No: 6): *TCTAGA*TACCCCCTTTCGTTTTATCTGT TTTTTTTTGGTGAACG TACCCCCTTTC GTTTTATCTGTTTTTTTTTGGTGAACGC *ATATG* | 1875 | 2027 |
| P3 | 4098 | SEQ ID No: 8 (identical to p2) | 4xVSV terminator, 16 nts spacers (SEQ ID No: 7): *TCTAGA*ATCCATG*ATATCT*GTTAGTTTT TTTCTACTAGAGTACTAGAG*TATCTGTT* AGTTTTTTTCTACTAGAGTACTAGAGTA TCTGTTAGTTTTTTTCTACTAGAGTACT AGAGTA*TCTGTT*AGTTTTTTTCTACTAG AG*CATATG* | 1875 | 2087 |
| p3-mod | 4092 | SEQ ID No: 9 Different from p2/p3 | 4xVSV terminator, 16 nts spacers (SEQ ID No: 7): *TCTAGA*ATCCATG*ATATCT*GTTAGTTTT TTTCTACTAGAGTACTAGAG*TATCTGTT* AGTTTTTTTCTACTAGAGTACTAGAGTA TCTGTTAGTTTTTTTCTACTAGAGTACT AGAGTA*TCTGTT*AGTTTTTTTCTACTAG AG*CATATG* | 1870 | na |

The ribozyme sequence with the indicated cleavage site is as follows for p2 and p3 (SEQ ID No: 8):

*GAATTC*CGTC'TAAGCGTGATACCCGCTTACTGAAGAGTCCCGTGAGGGAC
GAAACGGAATTGGATAC*TCTAGA*

The ribozyme sequence with the indicated cleavage site is as follows for p3-mod (SEQ ID No: 9):

*GAATT*'CAAGCGTGATACCCGCTTGCTGAAGAGTCCCGTGAGGGACGAAA
TTCTGGGGATAC*TCTAGA*

The sequence of the target RNA [mRNA sequence coding for *Photinus pyralis luciferase* (PpLuc)] is given in SEQ ID No. 10.

Rolling circle amplification (RCA): For the amplification of plasmid DNA by multiply-primed rolling circle amplification (RCA), the illustra TempliPhi Amplification Kit (GE Healthcare Life Science) was used according to the manufacturer's instructions with 200 ng of plasmid DNA in a total reaction volume of 200 μl. After incubation at 30° C. for 16 h, the RCA product was purified by phenol/chloroform extraction followed by precipitation with sodium acetate/ethanol.

Linearization of plasmids: For transcriptions from linear plasmids, the plasmid preparations were linearized with EcoRI or SspI (Thermo scientific) according to the manufacturer's recommendations and purified by isopropanol precipitation, washing with 75% ethanol (addition of 75% ethanol, centrifugation for 5 min with 16.000 g at 4° C., removal of the supernatant, centrifugation for 1 min at room temperature, removal of residual supernatant), drying and suspension in water for injection (Fresenius). The DNA concentration was determined by measuring the absorption at 260 nm.

In vitro transcription and purification: Unless otherwise stated, in vitro transcription reactions were performed with 0.05 g/L plasmid template at 37° C. in 80 mM HEPES/KOH, pH 7.5 containing 24 mM MgCl$_2$, 2 mM spermidine, 40 mM DTT, 5 U/ml pyrophosphatase (Thermo scientific), 200 U/ml Ribolock RNase inhibitor (Thermo scientific), 5000 U/ml T7 RNA polymerase (Thermo scientific), 5.8 mM G(5')ppp(5')G Cap analog, 4 mM ATP, UTP, CTP (each) and 1.45 mM GTP (all Thermo scientific). In some reactions, part of total concentrations of UTP and CTP were replaced with Pseudo UTP (pseudouridine-5'-triphosphate) and 5-methyl-CTP (5-methylcytidine-5'-triphosphate), respectively, as indicated below (both tebu-bio). In some reactions 0.025 g/L, 0.1 g/L, 0.15 g/L or 0.25 g/L plasmid template was used. The reaction volume was typically 20 μl. To stop the reaction, after 3 h, 100 U/μl DNaseI (Roche Life sciences) and 1 mM CaCl$_2$ were added and incubated at 37°

C. for 30 min at 37° C. RNA was precipitated with 2.86 M LiCl (16 h, −20° C.), followed by centrifugation (30 min, 16.000 g, 4° C.). Pellets were washed in 75% ethanol (five volumes of the transcription reaction, see linearization for details on the procedure), dried and dissolved in a volume of water for injection (Fresenius) corresponding to the original transcription reaction volume. The RNA concentration was determined by measuring the absorption at 260 nm. The yield is defined as the concentration of LiCl-precipitatable RNA formed during a transcription reaction.

Denaturing RNA agarose gel electrophoresis: To separate RNAs of different length under denaturing conditions, 1 μg of RNA (purified by LiCl precipitation) was denatured for 5 min at 80° C. in 0.2× gel loading buffer II (Life technologies) supplied with 0.001% ethidium bromide and applied to a 1.2% agarose gel (prepared in 1× MOPS buffer with 0.67% (V/V) formaldehyde and equilibrated in 1×MOPS with 0.74% formaldehyde). A voltage of 4.25 V/cm was applied for about 3 h or until the smallest marker fragment has migrated through 80% of the gel. The bands were visualized and photographed under UV light. The maximal exposure time was chosen so that no band was saturated.

Denaturing RNA acrylamide gel electrophoresis: For the analysis of short RNA by-products and their separation from the main RNA product, they were separated in 10% acrylamide/urea gels in tris-borate-EDTA-buffer (BioRad). 3.75 μg of total RNA were applied to each well of the gel after denaturation in 1× Gel Loading buffer II (Ambion) for 5 min at 80° C. The gel was run according to the manufacturer's recommendations and stained in 0.002% ethidium bromide for 10 minutes.

Calculation of the termination efficiency: RNA transcribed from SspI linearized plasmids was used to determine the termination efficiency of the terminator modules. Readthrough products can be seen in the gel as bands with lower electrophoretic mobility than the target RNA. First, the relative band intensity of each band was quantified. After inverting the colors, subtraction of the background and automatic band detection, the band intensities were calculated. This relative band intensity value is regarded as an approximate measure for the relative RNA mass present in each band. To convert this value into a measure for the relative molar quantity of RNA, the relative band intensity was normalized to the expected (Table 1) or approximated size (in nts) of the RNA (equal ethidium bromide binding assumed). For calculation of the termination efficiency on plasmid p1, equation (1) was used:

$$\text{int}_{norm}(\text{Target RNA})/\Sigma\text{int}_{norm}(\text{all bands})*100 \quad (1)$$

Figure 1:
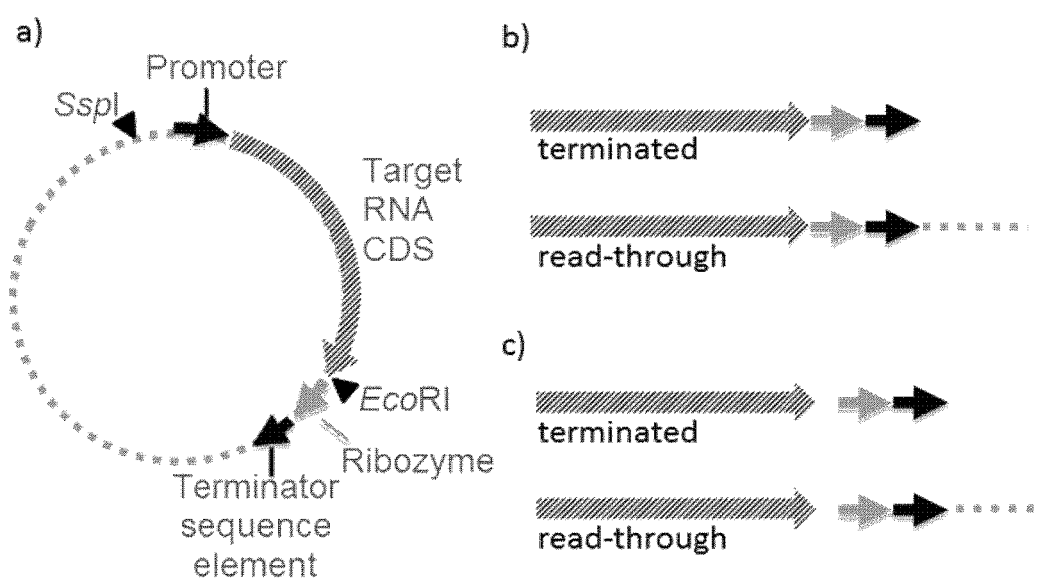
FIG. 1 Schematic depiction of the plasmid and the RNA-products

Read-through RNA from p2 and p3 are split by the ribozyme in one molecule of target RNA and one molecule of large read-through fragment (FIG. 1 and Table 1). Thus, the calculation of the termination efficiency was adjusted using equation (2):

$$[\text{int}_{norm}(\text{Target RNA},1875\text{ nts})-\text{int}_{norm}(\text{read-through fragment},2027/2087\text{ nts})]/\Sigma\text{int}_{norm}(\text{all bands})*100 \quad (2)$$

HPLC purification of RNA: HPLC purification of RNA was conducted according to WO2008077592. Briefly, 300 μg of RNA were diluted to 1800 μl 0.1 M TEAA and 1600 μl thereof injected onto a 50×7.5 mm PLRP-S column with 4000 Å pore size and 8 μm beads (Agilent Technologies) with a Summit HPLC device (Dionex).

Purification was performed with a linear gradient of acetonitrile in 0.1 M TEAA (pH~7). Typically fractions of 1 ml were collected and the two fractions with the highest absorption at 260 nm (A260) were pooled and precipitated in 0.25 M NaCl and 50% (V/V) isopropanole. The precipitate was washed twice with 75% ethanol, dried and dissolved in 50 μl of WFI.

Transfection into HeLa Cells: Cells were seeded in 96 well plates three days before transfection (10000 cells per well). Immediately before lipofection, cells were washed in opti-MEM. Cells were lipofected with 50 ng or 5 ng PpLuc-encoding mRNA complexed with Lipofectamine2000. mRNA coding for Renilla reniformis luciferase (RrLuc) was cotransfected together with PpLuc mRNA to control for transfection efficiency (2.5 ng or 0.25 ng of RrLuc mRNA per well). 24 hours after transfection, medium was aspirated and cells were lysed in 100 μl of lysis buffer (Passive Lysis Buffer, Promega). Lysates were stored at −80° C. until luciferase activity was measured.

Luciferase measurement: Luciferase activity was measured as relative light units (RLU) in a BioTek SynergyHT plate reader. PpLuc activity was measured at 5 seconds measuring time using 50 μl of lysate and 200 μl of luciferin buffer (75 μM luciferin, 25 mM Glycylglycin, pH 7.8 (NaOH), 15 mM MgSO4, 2 mM ATP). RrLuc activity was measured at 5 seconds measuring time using 50 μl of lysate and 200 μl of coelenterazin buffer (40 μM coelenterazin, 2.2 mM EDTA, 220 mM KH2PO4/K2HPO4 pH 5.0, 1.1 M NaCl, 1.3 mM NaN3, 0.44 g/l BSA).

Example 2

Transcription from Plasmid DNA Using Different Numbers of Termination Signals

The aim of this example was to find out whether transcription could efficiently be terminated using RNA polymerase termination signals.

As described in example 1, three different plasmids were produced that carry either one (p1), two (p2) or four (p3) terminator sequences: The VSV terminator sequence including extensions in p1 is described in Lyakhov et al. (J. Mol. Biol. (1998) 280, 201-213), the direct repeat of 1R11 in p2 is described in Kwon and Kang (J. Biol. Chem. 1999, 274:29149-29155); and the terminator sequence element comprising four VSV terminator sequences separated by spacers in p3 is described in Du et al. (Biotechnology and Bioengineering, Vol. 109, No. 4, April, 2012), wherein the additional eight nucleotides at the 5' end are described in Lyakhov et al. (J. Mol. Biol. (1998) 280, 201-213) and eight nucleotides of the spacer sequence were additionally added after the last VSV terminator sequence at the 3' end of the termination sequence in p3.

p1, p2 and p3 were linearized with SspI and a standard in vitro transcription was carried out. RNA was purified and separated, and the termination efficiency was determined as described in example 1.

FIG. 2 shows that the transcription was terminated in about 70% of the reactions using p1, i.e. a single VSV terminator, whereas the termination efficiency increased with an increasing number of terminator sequences to about 95%, see p2 and p3 in FIG. 2.

Example 3

Transcription from Circular DNA Using Different Template Concentrations

The aim of this example was to find out whether transcription would work using circular plasmid DNA, and what the yield of this reaction is compared to a standard reaction using linearized DNA.

p3 was linearized with EcoRI and a standard in vitro transcription using 0.05 g/L plasmid template as described in example 1 was carried out. This resulted in a yield of about 1.4 g/L RNA, see left lane of FIG. 3.

A standard in vitro transcription as described in example 1 using 0.05 g/L circular p3 was carried out. RNA was obtained, albeit at a lower yield compared to the linearized p3 as template, see lane 3 of FIG. 3. Several parameters of the standard in vitro transcription (excluding the template concentration) were modified in order to possibly increase the RNA yield. However, when changing these parameters, no significant increase in the RNA yield could be obtained. Surprisingly, it was then found that the template concentration is the key parameter for an increase in RNA yield. Thus, if the template concentration is lowered to 0.025 g/L, the RNA yield further decreases. If the concentration is increased to a range of from about 0.1 g/L to about 0.25 g/L, the RNA yield is comparable to the yield obtained using linearized DNA (see lanes 4 and 5 of FIG. 3).

The RNA products were further analyzed in a denaturing RNA agarose gel as described in example 1, and the results are shown in FIG. 4. As can be derived from FIG. 4, it was found that an increase in the circular DNA template concentration resulted in less low molecular weight RNAs and overall in a quality of the RNA similar to the quality obtained using linearized DNA.

Example 4

Transcription from the Product of RCA as DNA Template

The aim of this example was to find out whether transcription would work using the product of RCA as DNA template, and what the yield and RNA-composition of this reaction is compared to a standard reaction using linearized DNA. Briefly, RCA uses Phi DNA polymerase, random hexamer primers, nucleotides and a circular DNA as "input DNA". The random hexamer primers anneal to the input DNA at multiple sites and the DNA polymerase extends each of these primers. When the DNA polymerase reaches a downstream extended primer, strand displacement synthesis occurs, wherein the displaced strand is rendered single-stranded and available to be primed by more hexamer primers.

p3 was linearized with EcoRI and a standard in vitro transcription using 0.05 g/L plasmid template as described in example 1 was carried out. This resulted in a yield of about 1.4 g/L RNA, see left lane of FIG. 5a). 200 ng of p3 were used in a standard RCA assay as described in example 1 in order to obtain RCA product, which was subsequently purified. Purified RCA product was used as DNA template at a concentration of 0.05 g/L in a standard in vitro transcription assay as described in example 1. This resulted in a yield of about 1.5 g/L RNA, see right lane of FIG. 5a). The RNA products were further analyzed in a denaturing RNA agarose gel electrophoresis as described in example 1, and the results are shown in FIG. 5b).

The RNA yield using the RCA product as DNA template is surprisingly at least comparable if not superior over the use of linearized DNA, see FIG. 5a). As can be derived from FIG. 5b), there is no difference in the quality of RNA obtained using the linear DNA template (lin) or the RCA product (RCA) as DNA template.

Example 5

Transcription from Circular DNA Using Modified Nucleotides

The aim of this example was to find out whether the use of modified nucleotides might negatively influence i) the termination and ii) the ribozyme activity resulting in an increase in read-through products.

The in vitro transcriptions were carried out using the conditions described in example 1 for the modified nucleotides, wherein circular p3 was used as template and Pseudo-UTP (pseudouridine-5'-triphosphate) and/or 5-methyl-CTP (5-methylcytidine-5'-triphosphate) as modified nucleotides replaced UTP and/or CTP, respectively, to extents as indicated in FIG. 6b.

As can be derived from the gel in FIG. 6b, there was no negative effect on the termination, independent of the use and the concentration of modified nucleotides. It is noted that up to 100% Pseudo-UTP (pseudouridine-5'-triphosphate) or 5-methyl-CTP (5-methylcytidine-5'-triphosphate) or even 100% Pseudo-UTP (pseudouridine-5'-triphosphate) in combination with 100% 5-methyl-CTP (5-methylcytidine-5'-triphosphate) were used. Further, there was no substantial increase in read-through products. A general increase in electrophoretic mobility with increasing ratio of Pseudo-UTP (pseudouridine-5'-triphosphate) or 5-methyl-CTP (5-methylcytidine-5'-triphosphate) in the RNA was observed most probably due to an increase in charge.

Example 6

Purification of RNA Obtained Via Transcription from Circular DNA

The aim of this example was to find out whether the target RNA can efficiently be separated from other RNA sequences such as the ribozyme-sequence including the terminator sequence and potential read-through by-products.

p2 and p3 were used in this example, wherein p2 was either linearized with EcoRI or not, as indicated in FIG. 7. p3 was not linearized. Transcription reactions as described in example 1 were carried out (with 0.05 g/L linearized plasmid template or with 0.15 g/L circular template). The RNA was then further purified and samples of the purification steps were analyzed by gels as shown in FIG. 7: in lanes "Tsk", samples of the RNA directly after transcription were separated in either a 10% acrylamide/urea gel in TBE to analyze for the presence of small fragments (see FIG. 7, left side) or in a 1.2% agarose/formaldehyde gel in MOPS to analyze for the presence of large fragments (see FIG. 7, right side). For purification, the RNA was precipitated with LiCl, and samples thereof were also analyzed as described for the total RNA samples (see lanes "LiCl" in both gels of FIG. 7). Finally, HPLC purification was carried out and samples of the resulting final RNA were analyzed (see lanes "HPLC" in both gels of FIG. 7). The separation was carried out using the HPLC purification method as described in example 1.

FIG. 7 shows that the RNA can very efficiently be separated from by-products and smaller fragments corresponding to the ribozyme-sequences by HPLC.

Example 7

Expression Capability of RNA Produced from Circular DNA

Since the ribozyme cleaves at its 5'-end, the resulting target RNA has a 2'3' cyclic phosphate at its 3' end and the question arises whether this has any influence on the expression capability. The aim of this example was to find out whether there is any difference in the expression capability of RNA produced using circular DNA as template compared to RNA produced from linearized DNA as template.

In order to investigate this, p3 with DNA coding for luciferase was linearized with EcoRI and luciferase-mRNA was produced by in vitro transcription as outlined in example 1. It is noted that the RNA produced thereby ends with the nucleotides GAAUU (see Table 1). p3-mod was used as circular template to produce luciferase-RNA as outlined in example 1, wherein 0.15 g/L circular plasmid was used as DNA template. It is noted that the RNA also ends with the nucleotides GAAUU to have exactly identical 3' sequence endings (see also Table 1). The HPLC purified RNAs were each transfected according to standard methods into HeLa cells and the luciferase activity as measure of luciferase expression from the RNAs was independently determined for each RNA according to standard methods as described in example 1.

As can be derived from FIG. 8, RNA produced from circular p3-mod (white bar) showed comparable expression capability as RNA produced from linear p3 (black bar). Accordingly, the 2'3' cyclic phosphate present in the RNA produced from circular p3-mod did not decrease the expression capability. Overall, RNA produced from circular plasmids can be used to induce comparable expression in transfected HeLa cells.

The invention claimed is:

1. A method of producing a linear target RNA comprising the steps of:
   a) providing a circular DNA as template DNA comprising the following sequence elements from 5' to 3':
      i. an RNA polymerase promoter sequence operably linked to
      ii. a sequence encoding said target RNA operably linked to
      iii. a sequence encoding a self-cleaving ribozyme, wherein said self-cleaving ribozyme cleaves close to or at its 5' end, operably linked to
      iv. an RNA polymerase terminator sequence element; and
   b) in vitro transcribing said template DNA to obtain said target RNA;
   c) purifying said target RNA by at least one purification step in order to obtain purified target RNA;
   wherein said method does not comprise a step of linearizing said circular DNA provided in step a),
   wherein said RNA polymerase terminator sequence element comprises at least two Class II termination sequences.

2. The method of claim 1, wherein the RNA polymerase terminator sequence element comprises at least two Class II termination sequences and does not comprise a Class I termination sequence.

3. The method of claim 1, wherein the RNA polymerase terminator sequence element comprises at least one VSV terminator sequence or at least one 1R11 variant rrnB T1 downstream terminator sequence.

4. The method of claim 1, wherein the in vitro transcription is carried out in the presence of naturally occurring nucleotides and at least one modified nucleotide, wherein said at least one modified nucleotide at least partially replaces at least one naturally occurring nucleotide.

5. The method of claim 1, wherein the in vitro transcription is carried out in the presence of a cap analog.

6. The method of claim 1, wherein said target RNA is purified by at least one first and at least one second purification step.

7. The method of claim 6, wherein the at least one first purification step comprises a precipitation step, and the at least one second purification step comprises a chromatographic step.

8. The method of claim 7, wherein the at least one first purification step comprises an alcohol precipitation step or a LiCl precipitation step, and the at least one second purification step comprises a chromatographic step selected from the group consisting of HPLC, anion exchange chromatography, affinity chromatography, hydroxyapatite chromatography and core bead chromatography.

9. The method of claim 6, wherein the at least one first purification step comprises a tangential flow filtration step, and the at least one second purification step comprises a chromatographic step.

10. The method of claim 9, wherein the at least one first purification step comprises a diafiltration step using tangential flow filtration or a concentration step using tangential flow filtration, and the at least one second purification step comprises a chromatographic step selected from the group consisting of HPLC, anion exchange chromatography, affinity chromatography, hydroxyapatite chromatography and core bead chromatography.

11. The method of claim 1, wherein said circular DNA provided in step a) is amplified by rolling circle amplification prior to the in vitro transcription in step b).

12. The method of claim 1, wherein said method does not comprise a step of amplifying said circular DNA, and said circular DNA is provided in step a) at a concentration ranging from about 0.075 g/L to about 0.3 g/L.

13. The method of claim 1, wherein said RNA polymerase promoter sequence is a T7 RNA polymerase promoter sequence.

14. The method of claim 1, wherein said target RNA is selected from the group consisting of mRNA, viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

15. The method of claim 1, wherein said self-cleaving ribozyme encoded in sequence element c) is selected from the group consisting of a hepatitis delta virus (HDV) ribozyme, a hammerhead ribozyme and a hairpin ribozyme.

16. The method of claim 1, wherein said Class II termination sequences are selected from the group consisting of the VSV terminator sequence, the PTH terminator sequence, the rrnB T1 downstream terminator sequence, the rrnC terminator sequence, the concatemer junction sequence of the replicating T7 DNA, and a variant of any of the foregoing.

17. The method of claim 1, wherein said Class II termination sequences are identical.

18. The method of claim 17, wherein said Class II termination sequences are VSV terminator sequences or 1R11 variant rrnB TI downstream terminator sequences.

19. The method of claim 1, wherein the purified target RNA does not comprise a self-cleaving ribozyme sequence.

\* \* \* \* \*

SEQUENCE LISTING

```
<160> NUMBER OF SEQ ID NOS: 40

<210> SEQ ID NO 1
<211> LENGTH: 3941
<212> TYPE: DNA
<213> ORGANISM: Artificial Sequence
<220> FEATURE:
<223> OTHER INFORMATION: Plasmid p1

<400> SEQUENCE: 1
catgtgagca aaaggccagc aaaaggccag gaaccgtaaa aaggccgcgt tgctggcgtt     60
tttccatagg ctccgccccc ctgacgagca tcacaaaaat cgacgctcaa gtcagaggtg    120
gcgaaacccg acaggactat aaagatacca ggcgtttccc cctggaagct ccctcgtgcg    180
ctctcctgtt ccgaccctgc cgcttaccgg atacctgtcc gcctttctcc cttcgggaag    240
cgtggcgctt tctcatagct cacgctgtag gtatctcagt tcggtgtagg tcgttcgctc    300
caagctgggc tgtgtgcacg aaccccccgt tcagcccgac cgctgcgcct tatccggtaa    360
ctatcgtctt gagtccaacc cggtaagaca cgacttatcg ccactggcag cagccactgg    420
taacaggatt agcagagcga ggtatgtagg cggtgctaca gagttcttga agtggtggcc    480
taactacggc tacactagaa gaacagtatt tggtatctgc gctctgctga gccagttac     540 cttcggaaaa agagttggta gctcttgatc cggcaaacaa accaccgctg gtagcggtgg    600
tttttttgtt tgcaagcagc agattacgcg cagaaaaaaa ggatctcaag aagatccttt    660
gatcttttct acggggtctg acgctcagtg gaacgaaaac tcacgttaag ggattttggt    720
catgagatta tcaaaaagga tcttcaccta gatcctttta aattaaaaat gaagttttaa    780
atcaatctaa agtatatatg agtaaacttg gtctgacagt taccaatgct taatcagtga    840
ggcacctatc tcagcgatct gtctatttcg ttcatccata gttgcctgac tccccgtcgt    900
gtagataact acgatacggg agggcttacc atctggcccc agtgctgcaa tgataccgcg    960
agacccacgc tcaccggctc cagatttatc agcaataaac cagccagccg gaagggccga   1020
gcgcagaagt ggtcctgcaa ctttatccgc ctccatccag tctattaatt gttgccggga   1080
agctagagta agtagttcgc cagttaatag tttgcgcaac gttgttgcca ttgctacagg   1140
catcgtggtg tcacgctcgt cgtttggtat ggcttcattc agctccggtt cccaacgatc   1200
aaggcgagtt acatgatccc ccatgttgtg caaaaaagcg gttagctcct tcggtcctcc   1260
gatcgttgtc agaagtaagt tggccgcagt gttatcactc atggttatgg cagcactgca   1320
taattctctt actgtcatgc catccgtaag atgcttttct gtgactggtg agtactcaac   1380
caagtcattc tgagaatagt gtatgcggcg accgagttgc tcttgcccgg cgtcaatacg   1440
ggataatacc gcgccacata gcagaacttt aaaagtgctc atcattggaa aacgttcttc   1500
```

```
ggggcgaaaa ctctcaagga tcttaccgct gttgagatcc agttcgatgt aacccactcg    1560
tgcacccaac tgatcttcag catcttttac tttcaccagc gtttctgggt gagcaaaaac    1620
aggaaggcaa aatgccgcaa aaagggaat aagggcgaca cggaaatgtt gaatactcat     1680
actcttcctt tttcaatatt attgaagcat ttatcagggt tattgtctca tgagcggata    1740
catatttgaa tgtatttaga aaaataaaca ataggggtt ccgcgcacat ttccccgaaa     1800
agtgccacct gacgtctaat acgactcact atagggagaa agcttaccat ggaggacgcc    1860
aagaacatca agaagggccc ggcgcccttc tacccgctgg aggacgggac cgccggcgag    1920
cagctccaca aggccatgaa gcggtacgcc ctggtgccgg cgacgatcgc cttcaccgac    1980
gcccacatcg aggtcgacat cacctacgcg gagtacttcg agatgagcgt gcgcctggcc    2040
gaggccatga agcggtacgg cctgaacacc aaccaccgga tcgtggtgtg ctcggagaac    2100
agcctgcagt tcttcatgcc ggtgctgggc gccctcttca tcggcgtggc cgtcgccccg    2160
gcgaacgaca tctacaacga gcgggagctg ctgaacagca tggggatcag ccagccgacc    2220
gtggtgttcg tgagcaagaa gggcctgcag aagatcctga acgtgcagaa gaagctgccc    2280
atcatccaga gatcatcat catggacagc aagaccgact accagggctt ccagtcgatg    2340
tacacgttcg tgaccagcca cctcccgccg ggcttcaacg agtacgactt cgtcccggag    2400
agcttcgacc gggacaagac catcgccctg atcatgaaca gcagcggcag caccggcctg    2460 ccgaagggg tggccctgcc gcaccggacc gcctgcgtgc gcttctcgca cgcccgggac    2520
cccatcttcg gcaaccagat catcccgac accgccatcc tgagcgtggt gccgttccac    2580
cacggcttcg gcatgttcac gaccctgggc tacctcatct gcggcttccg ggtggtcctg    2640
atgtaccggt tcgaggagga gctgttcctg cggagcctgc aggactacaa gatccagagc    2700
gcgctgctcg tgccgaccct gttcagcttc ttcgccaaga gcaccctgat cgacaagtac    2760
gacctgtcga acctgcacga gatcgccagc ggggcgccc cgctgagcaa ggaggtgggc    2820
gaggccgtgg ccaagcggtt ccacctcccg ggcatccgcc agggctacgg cctgaccgag    2880
accacgagcg cgatcctgat cacccccgag ggggacgaca gccgggcgc cgtgggcaag    2940 gtggtcccgt tcttcgaggc caaggtggtg gacctgacca ccggcaagac cctgggcgtg    3000
aaccagcggg gcgagctgtg cgtgcggggg ccgatgatca tgagcggcta cgtgaacaac    3060
ccggaggcca ccaacgccct catcgacaag gacggctggc tgcacagcgg cgacatcgcc    3120
tactgggacg aggacgagca cttcttcatc gtcgaccggc tgaagtcgct gatcaagtac    3180
aagggctacc aggtggcgcc ggccgagctg gagagcatcc tgctccagca ccccaacatc    3240
ttcgacgccg gcgtggccgg gctgccggac gacgacgccg gcgagctgcc ggccgcggtg    3300
gtggtgctgg agcacggcaa gaccatgacg gagaaggaga tcgtcgacta cgtggccagc    3360
caggtgacca ccgccaagaa gctgcggggc ggcgtggtgt tcgtggacga ggtcccgaag    3420
ggcctgaccg gaagctcga cgcccggaag atccgcgaga tcctgatcaa ggccaagaag    3480
ggcggcaaga tcgccgtgtg aggactagtt ataagactga ctagcccgat gggcctccca    3540
acgggccctc ctcccctcct tgcaccgaga ttaataaaaa aaaaaaaaaa aaaaaaaaa    3600 aaaaaaaaaa aaaaaaaaaa aaaaaaaaaa aaaaaaaat gcatcccccc cccccccccc    3660
cccccccccc ccccaaagg ctcttttcag agccaccaga attcggatac tctagaatcc    3720
atgatatctg ttagttttttt tctactagag catatgctta agcagctgca ttaatgaatc    3780
ggccaacgcg cggggagagg cggtttgcgt attgggcgct cttccgcttc ctcgctcact    3840
```

| | |
|---|---|
| gactcgctgc gctcggtcgt tcggctgcgg cgagcggtat cagctcactc aaaggcggta | 3900 |
| atacggttat ccacagaatc aggggataac gcaggaaaga a | 3941 |

<210> SEQ ID NO 2
<211> LENGTH: 4038
<212> TYPE: DNA
<213> ORGANISM: Artificial Sequence
<220> FEATURE:
<223> OTHER INFORMATION: Plasmid p2

<400> SEQUENCE: 2

| | |
|---|---|
| catgtgagca aaaggccagc aaaaggccag gaaccgtaaa aaggccgcgt tgctggcgtt | 60 |
| tttccatagg ctccgccccc ctgacgagca tcacaaaaat cgacgctcaa gtcagaggtg | 120 |
| gcgaaacccg acaggactat aaagatacca ggcgtttccc cctggaagct ccctcgtgcg | 180 |
| ctctcctgtt ccgaccctgc cgcttaccgg atacctgtcc gcctttctcc cttcgggaag | 240 |
| cgtggcgctt tctcatagct cacgctgtag gtatctcagt tcggtgtagg tcgttcgctc | 300 |
| caagctgggc tgtgtgcacg aaccccccgt tcagcccgac cgctgcgcct tatccggtaa | 360 |
| ctatcgtctt gagtccaacc cggtaagaca cgacttatcg ccactggcag cagccactgg | 420 |
| taacaggatt agcagagcga ggtatgtagg cggtgctaca gagttcttga agtggtggcc | 480 |
| taactacggc tacactagaa gaacagtatt tggtatctgc gctctgctga agccagttac | 540 |
| cttcggaaaa agagttggta gctcttgatc cggcaaacaa accaccgctg gtagcggtgg | 600 |
| tttttttgtt tgcaagcagc agattacgcg cagaaaaaaa ggatctcaag aagatccttt | 660 |
| gatcttttct acggggtctg acgctcagtg gaacgaaaac tcacgttaag ggattttggt | 720 |
| catgagatta tcaaaaagga tcttcaccta gatcctttta aattaaaaat gaagttttaa | 780 |
| atcaatctaa agtatatatg agtaaacttg gtctgacagt taccaatgct taatcagtga | 840 |
| ggcacctatc tcagcgatct gtctatttcg ttcatccata gttgcctgac tccccgtcgt | 900 |
| gtagataact acgatacggg agggcttacc atctggcccc agtgctgcaa tgataccgcg | 960 |
| agacccacgc tcaccggctc cagatttatc agcaataaac cagccagccg aagggccga | 1020 |
| gcgcagaagt ggtcctgcaa ctttatccgc ctccatccag tctattaatt gttgccggga | 1080 |
| agctagagta agtagttcgc cagttaatag tttgcgcaac gttgttgcca ttgctacagg | 1140 |
| catcgtggtg tcacgctcgt cgtttggtat ggcttcattc agctccggtt cccaacgatc | 1200 |
| aaggcgagtt acatgatccc ccatgttgtg caaaaaagcg gttagctcct tcggtcctcc | 1260 |
| gatcgttgtc agaagtaagt tggccgcagt gttatcactc atggttatgg cagcactgca | 1320 |
| taattctctt actgtcatgc catccgtaag atgcttttct gtgactggtg agtactcaac | 1380 |
| caagtcattc tgagaatagt gtatgcggcg accgagttgc tcttgcccgg cgtcaatacg | 1440 |
| ggataatacc gcgccacata gcagaacttt aaaagtgctc atcattggaa aacgttcttc | 1500 |
| ggggcgaaaa ctctcaagga tcttaccgct gttgagatcc agttcgatgt aacccactcg | 1560 |
| tgcacccaac tgatcttcag catctttac tttcaccagc gtttctgggt gagcaaaaac | 1620 |
| aggaaggcaa aatgccgcaa aaaagggaat aagggcgaca cggaaatgtt gaatactcat | 1680 |
| actcttcctt tttcaatatt attgaagcat ttatcagggt tattgtctca tgagcggata | 1740 |
| catatttgaa tgtatttaga aaaataaaca ataggggtt ccgcgcacat ttccccgaaa | 1800 |
| agtgccacct gacgtctaat acgactcact ataggagaa agcttaccat ggaggacgcc | 1860 |
| aagaacatca gaagggcccc ggcgcccttc tacccgctgg aggacgggac cgccggcgag | 1920 |
| cagctccaca aggccatgaa gcggtacgcc ctggtgccgg gcacgatcgc cttcaccgac | 1980 |

```
gcccacatcg aggtcgacat cacctacgcg gagtacttcg agatgagcgt gcgcctggcc    2040
gaggccatga agcggtacgg cctgaacacc aaccaccgga tcgtggtgtg ctcggagaac    2100
agcctgcagt tcttcatgcc ggtgctgggc gccctcttca tcggcgtggc cgtcgccccg    2160
gcgaacgaca tctacaacga gcgggagctg ctgaacagca tggggatcag ccagccgacc    2220
gtggtgttcg tgagcaagaa gggcctgcag aagatcctga acgtgcagaa gaagctgccc    2280
atcatccaga agatcatcat catggacagc aagaccgact accagggctt ccagtcgatg    2340
tacacgttcg tgaccagcca cctcccgccg ggcttcaacg agtacgactt cgtcccggag    2400
agcttcgacc gggacaagac catcgccctg atcatgaaca gcagcggcag caccggcctg    2460 ccgaagggg tggccctgcc gcaccggacc gcctgcgtgc gcttctcgca cgcccgggac    2520
cccatcttcg gcaaccagat catcccggac accgccatcc tgagcgtggt gccgttccac    2580
cacggcttcg gcatgttcac gaccctgggc tacctcatct gcggcttccg ggtggtcctg    2640
atgtaccggt tcgaggagga gctgttcctg cggagcctgc aggactacaa gatccagagc    2700
gcgctgctcg tgccgaccct gttcagcttc ttcgccaaga gcaccctgat cgacaagtac    2760
gacctgtcga acctgcacga gatcgccagc ggggcgccc cgctgagcaa ggaggtgggc    2820
gaggccgtgg ccaagcggtt ccacctcccg ggcatccgcc agggctacgg cctgaccgag    2880
accacgagcg cgatcctgat cacccccgag ggggacgaca gccgggcgc cgtgggcaag    2940 gtggtcccgt tcttcgaggc caaggtggtg gacctggaca ccggcaagac cctgggcgtg    3000
aaccagcggg gcgagctgtg cgtgcggggg ccgatgatca tgagcggcta cgtgaacaac    3060
ccggaggcca ccaacgccct catcgacaag gacggctggc tgcacagcgg cgacatcgcc    3120
tactgggacg aggacgagca cttcttcatc gtcgaccggc tgaagtcgct gatcaagtac    3180
aagggctacc aggtggcgcc ggccgagctg gagagcatcc tgctccagca ccccaacatc    3240
ttcgacgccg gcgtggccgg gctgccggac gacgacgccg gcgagctgcc ggccgcggtg    3300
gtggtgctgg agcacggcaa gaccatgacg gagaaggaga tcgtcgacta cgtggccagc    3360
caggtgacca ccgccaagaa gctgcggggc ggcgtggtgt tcgtggacga ggtcccgaag    3420
ggcctgaccg ggaagctcga cgcccggaag atccgcgaga tcctgatcaa ggccaagaag    3480
ggcggcaaga tcgccgtgtg aggactagtt ataagactga ctagcccgat gggcctccca    3540
acgggccctc ctcccctcct tgcaccgaga ttaataaaaa aaaaaaaaa aaaaaaaaa    3600 aaaaaaaaaa aaaaaaaaaa aaaaaaaaaa aaaaaaaat gcatcccccc cccccccccc    3660
cccccccccc ccccaaagg ctcttttcag agccaccaga attccgtcta agcgtgatac    3720
ccgcttactg aagagtcccg tgagggacga acggaattg gatactctag ataccccctt    3780
tcgttttatc tgtttttttt tggtgaacgt acccccttc gttttatctg ttttttttg    3840 gtgaacgcat atgcttaagc agctgcatta atgaatcggc caacgcgcgg ggagaggcgg    3900
tttgcgtatt gggcgctctt ccgcttcctc gctcactgac tcgctgcgct cggtcgttcg    3960
gctgcggcga gcggtatcag ctcactcaaa ggcggtaata cggttatcca cagaatcagg    4020
ggataacgca ggaaagaa                                                  4038
```

<210> SEQ ID NO 3  
<211> LENGTH: 4098  
<212> TYPE: DNA  
<213> ORGANISM: Artificial Sequence  
<220> FEATURE:  
<223> OTHER INFORMATION: plasmid p3

-continued

```
<400> SEQUENCE: 3
catgtgagca aaaggccagc aaaaggccag gaaccgtaaa aaggccgcgt tgctggcgtt      60
tttccatagg ctccgccccc ctgacgagca tcacaaaaat cgacgctcaa gtcagaggtg     120
gcgaaacccg acaggactat aaagatacca ggcgtttccc cctggaagct ccctcgtgcg     180
ctctcctgtt ccgaccctgc cgcttaccgg atacctgtcc gcctttctcc cttcgggaag     240
cgtggcgctt tctcatagct cacgctgtag gtatctcagt tcggtgtagg tcgttcgctc     300
caagctgggc tgtgtgcacg aaccccccgt tcagcccgac cgctgcgcct tatccggtaa     360
ctatcgtctt gagtccaacc cggtaagaca cgacttatcg ccactggcag cagccactgg     420
taacaggatt agcagagcga ggtatgtagg cggtgctaca gagttcttga agtggtggcc     480
taactacggc tacactagaa gaacagtatt tggtatctgc gctctgctga agccagttac     540
cttcggaaaa agagttggta gctcttgatc cggcaaacaa accaccgctg gtagcggtgg     600
tttttttgtt tgcaagcagc agattacgcg cagaaaaaaa ggatctcaag aagatccttt     660
gatcttttct acggggtctg acgctcagtg gaacgaaaac tcacgttaag ggattttggt     720
catgagatta tcaaaaagga tcttcaccta gatcctttta aattaaaaat gaagttttaa     780
atcaatctaa agtatatatg agtaaacttg gtctgacagt taccaatgct taatcagtga     840
ggcacctatc tcagcgatct gtctatttcg ttcatccata gttgcctgac tccccgtcgt     900
gtagataact acgatacggg agggcttacc atctggcccc agtgctgcaa tgataccgcg     960
agacccacgc tcaccggctc cagatttatc agcaataaac cagccagccg aagggccga    1020 gcgcagaagt ggtcctgcaa ctttatccgc ctccatccag tctattaatt gttgccggga    1080
agctagagta agtagttcgc cagttaatag tttgcgcaac gttgttgcca ttgctacagg    1140
catcgtggtg tcacgctcgt cgtttggtat ggcttcattc agctccggtt cccaacgatc    1200
aaggcgagtt acatgatccc ccatgttgtg caaaaaagcg gttagctcct tcggtcctcc    1260
gatcgttgtc agaagtaagt tggccgcagt gttatcactc atggttatgg cagcactgca    1320
taattctctt actgtcatgc catccgtaag atgcttttct gtgactggtg agtactcaac    1380
caagtcattc tgagaatagt gtatgcggcg accgagttgc tcttgcccgg cgtcaatacg    1440
ggataatacc gcgccacata gcagaacttt aaaagtgctc atcattggaa aacgttcttc    1500
ggggcgaaaa ctctcaagga tcttaccgct gttgagatcc agttcgatgt aacccactcg    1560
tgcacccaac tgatcttcag catcttttac tttcaccagc gtttctgggt gagcaaaaac    1620
aggaaggcaa aatgccgcaa aaaagggaat aagggcgaca cggaaatgtt gaatactcat    1680
actcttcctt tttcaatatt attgaagcat ttatcagggt tattgtctca tgagcggata    1740
catatttgaa tgtatttaga aaataaaca aataggggtt ccgcgcacat ttccccgaaa    1800
agtgccacct gacgtctaat acgactcact atagggagaa agcttaccat ggaggacgcc    1860
aagaacatca agaagggccc ggcgcccttc tacccgctgg aggacgggac cgccggcgag    1920
cagctccaca aggccatgaa gcggtacgcc ctggtgccgg cacgatcgc cttcaccgac    1980 gcccacatcg aggtcgacat cacctacgcg gagtacttcg agatgagcgt gcgcctggcc    2040
gaggccatga gcggtacgg cctgaacacc aaccaccgga tcgtggtgtg ctcggagaac    2100
agcctgcagt tcttcatgcc ggtgctgggc gccctcttca tcggcgtggc cgtcgccccg    2160
gcgaacgaca tctacaacga gcgggagctg ctgaacagca tggggatcag ccagcccacc    2220
gtggtgttcg tgagcaagaa gggcctgcag aagatcctga acgtgcagaa gaagctgccc    2280
atcatccaga agatcatcat catggacagc aagaccgact accagggctt ccagtcgatg    2340
```

```
tacacgttcg tgaccagcca cctcccgccg ggcttcaacg agtacgactt cgtcccggag    2400
agcttcgacc gggacaagac catcgccctg atcatgaaca gcagcggcag caccggcctg    2460 ccgaagggg tggccctgcc gcaccggacc gcctgcgtgc gcttctcgca cgcccgggac     2520
cccatcttcg gcaaccagat catcccggac accgccatcc tgagcgtggt gccgttccac    2580
cacggcttcg gcatgttcac gaccctgggc tacctcatct gcggcttccg ggtggtcctg    2640
atgtaccggt tcgaggagga gctgttcctg cggagcctgc aggactacaa gatccagagc    2700
gcgctgctcg tgccgaccct gttcagcttc ttcgccaaga gcaccctgat cgacaagtac    2760
gacctgtcga acctgcacga gatcgccagc gggggcgccc gctgagcaa ggaggtgggc     2820 gaggccgtgg ccaagcggtt ccacctcccg gcatccgcc agggctacgg cctgaccgag     2880
accacgagcg cgatcctgat cacccccgag ggggacgaca gcccgggcgc cgtgggcaag    2940
gtggtcccgt tcttcgaggc caaggtggtg gacctggaca ccggcaagac cctgggcgtg    3000
aaccagcggg gcgagctgtg cgtgcggggg ccgatgatca tgagcggcta cgtgaacaac    3060
ccggaggcca ccaacgccct catcgacaag gacggctggc tgcacagcgg cgacatcgcc    3120
tactgggacg aggacgagca cttcttcatc gtcgaccggc tgaagtcgct gatcaagtac    3180
aagggctacc aggtggcgcc ggccgagctg gagagcatcc tgctccagca ccccaacatc    3240
ttcgacgccg gcgtggccgg gctgccggac gacgacgccg gcgagctgcc ggccgcggtg    3300
gtggtgctgg agcacggcaa gaccatgacg gagaaggaga tcgtcgacta cgtggccagc    3360
caggtgacca ccgccaagaa gctgcggggc ggcgtggtgt tcgtggacga ggtcccgaag    3420
ggcctgaccg ggaagctcga cgcccggaag atccgcgaga tcctgatcaa ggccaagaag    3480
ggcggcaaga tcgccgtgtg aggactagtt ataagactga ctagcccgat gggcctccca    3540
acgggccctc ctcccctcct tgcaccgaga ttaataaaaa aaaaaaaaaa aaaaaaaaa     3600 aaaaaaaaa aaaaaaaaaa aaaaaaaaaa aaaaaaaat gcatccccc cccccccccc      3660 cccccccccc ccccaaagg ctcttttcag agccaccaga attccgtcta agcgtgatac     3720
ccgcttactg aagagtcccg tgagggacga aacggaattg gatactctag aatccatgat    3780
atctgttagt tttttctac tagagtacta gagtatctgt tagtttttt ctactagagt      3840 actagagtat ctgttagttt ttttctacta gagtactaga gtatctgtta gttttttct    3900 actagagcat atgcttaagc agctgcatta atgaatcggc caacgcgcgg ggagaggcgg    3960
tttgcgtatt gggcgctctt ccgcttcctc gctcactgac tcgctgcgct cggtcgttcg    4020
gctgcggcga gcggtatcag ctcactcaaa ggcggtaata cggttatcca cagaatcagg    4080
ggataacgca ggaaagaa                                                   4098
```

<210> SEQ ID NO 4
<211> LENGTH: 4092
<212> TYPE: DNA
<213> ORGANISM: Artificial Sequence
<220> FEATURE:
<223> OTHER INFORMATION: Plasmid p3-mod

<400> SEQUENCE: 4

```
catgtgagca aaaggccagc aaaaggccag gaaccgtaaa aaggccgcgt tgctggcgtt    60
tttccatagg ctccgccccc ctgacgagca tcacaaaaat cgacgctcaa gtcagaggtg    120
gcgaaacccg acaggactat aaagatacca ggcgtttccc cctggaagct ccctcgtgcg    180
ctctcctgtt ccgaccctgc cgcttaccgg atacctgtcc gcctttctcc cttcgggaag    240
```

```
cgtggcgctt tctcatagct cacgctgtag gtatctcagt tcggtgtagg tcgttcgctc    300
caagctgggc tgtgtgcacg aaccccccgt tcagcccgac cgctgcgcct tatccggtaa    360
ctatcgtctt gagtccaacc cggtaagaca cgacttatcg ccactggcag cagccactgg    420
taacaggatt agcagagcga ggtatgtagg cggtgctaca gagttcttga agtggtggcc    480
taactacggc tacactagaa gaacagtatt tggtatctgc gctctgctga agccagttac    540
cttcggaaaa agagttggta gctcttgatc cggcaaacaa accaccgctg gtagcggtgg    600
tttttttgtt tgcaagcagc agattacgcg cagaaaaaaa ggatctcaag aagatccttt    660
gatcttttct acggggtctg acgctcagtg gaacgaaaac tcacgttaag ggattttggt    720
catgagatta tcaaaaagga tcttcaccta gatcctttta aattaaaaat gaagttttaa    780
atcaatctaa agtatatatg agtaaacttg gtctgacagt taccaatgct taatcagtga    840
ggcacctatc tcagcgatct gtctatttcg ttcatccata gttgcctgac tccccgtcgt    900
gtagataact acgatacggg agggcttacc atctggcccc agtgctgcaa tgataccgcg    960
agacccacgc tcaccggctc cagatttatc agcaataaac cagccagccg gaagggccga   1020
gcgcagaagt ggtcctgcaa ctttatccgc ctccatccag tctattaatt gttgccggga   1080
agctagagta agtagttcgc cagttaatag tttgcgcaac gttgttgcca ttgctacagg   1140
catcgtggtg tcacgctcgt cgtttggtat ggcttcattc agctccggtt cccaacgatc   1200
aaggcgagtt acatgatccc ccatgttgtg caaaaaagcg gttagctcct tcggtcctcc   1260
gatcgttgtc agaagtaagt tggccgcagt gttatcactc atggttatgg cagcactgca   1320
taattctctt actgtcatgc catccgtaag atgcttttct gtgactggtg agtactcaac   1380
caagtcattc tgagaatagt gtatgcggcg accgagttgc tcttgcccgg cgtcaatacg   1440
ggataatacc gcgccacata gcagaacttt aaaagtgctc atcattggaa aacgttcttc   1500
ggggcgaaaa ctctcaagga tcttaccgct gttgagatcc agttcgatgt aacccactcg   1560
tgcacccaac tgatcttcag catcttttac tttcaccagc gtttctgggt gagcaaaaac   1620
aggaaggcaa aatgccgcaa aaaagggaat aagggcgaca cggaaatgtt gaatactcat   1680
actcttcctt tttcaatatt attgaagcat ttatcagggt tattgtctca tgagcggata   1740
catatttgaa tgtatttaga aaaataaaca ataggggtt ccgcgcacat ttccccgaaa   1800
agtgccacct gacgtctaat acgactcact atagggagaa agcttaccat ggaggacgcc   1860
aagaacatca agaagggccc ggcgcccttc tacccgctgg aggacgggac cgccggcgag   1920
cagctccaca aggccatgaa gcggtacgcc ctggtgccgg gcacgatcgc cttcaccgac   1980
gcccacatcg aggtcgacat cacctacgcg gagtacttcg agatgagcgt gcgcctggcc   2040
gaggccatga gcggtacgg cctgaacacc aaccaccgga tcgtggtgtg ctcggagaac   2100
agcctgcagt tcttcatgcc ggtgctgggc gccctcttca tcggcgtggc cgtcgccccg   2160
gcgaacgaca tctacaacga gcgggagctg ctgaacagca tggggatcag ccagcccacc   2220
gtggtgttcg tgagcaagaa gggcctgcag aagatcctga acgtgcagaa gaagctgccc   2280
atcatccaga gatcatcat catggacagc aagaccgact accagggctt ccagtcgatg   2340
tacacgttcg tgaccagcca cctccccgcg ggcttcaacg agtacgactt cgtcccggag   2400
agcttcgacc gggacaagac catcgccctg atcatgaaca gcagcggcag caccggcctg   2460
ccgaaggggg tggccctgcc gcaccggacc gcctgcgtgc gcttctcgca cgcccgggac   2520
cccatcttcg gcaaccagat catcccggac accgccatcc tgagcgtggt gccgttccac   2580
cacggcttcg gcatgttcac gaccctgggc tacctcatct gcggcttccg ggtggtcctg   2640
```

```
atgtaccggt tcgaggagga gctgttcctg cggagcctgc aggactacaa gatccagagc    2700
gcgctgctcg tgccgaccct gttcagcttc ttcgccaaga gcaccctgat cgacaagtac    2760
gacctgtcga acctgcacga gatcgccagc gggggcgccc cgctgagcaa ggaggtgggc    2820
gaggccgtgg ccaagcggtt ccacctcccg ggcatccgcc agggctacgg cctgaccgag    2880
accacgagcg cgatcctgat cacccccgag ggggacgaca agccgggcgc cgtgggcaag    2940
gtggtcccgt tcttcgaggc caaggtggtg gacctgaca ccggcaagac cctgggcgtg     3000
aaccagcggg gcgagctgtg cgtgcggggg ccgatgatca tgagcggcta cgtgaacaac    3060
ccggaggcca ccaacgccct catcgacaag gacggctggc tgcacagcgg cgacatcgcc    3120
tactgggacg aggacgagca cttcttcatc gtcgaccggc tgaagtcgct gatcaagtac    3180
aagggctacc aggtggcgcc ggccgagctg gagagcatcc tgctccagca ccccaacatc    3240
ttcgacgccg cgtggccgg gctgccggac gacgacgccg gcgagctgcc ggccgcggtg     3300
gtggtgctgg agcacggcaa gaccatgacg gagaaggaga tcgtcgacta cgtggccagc    3360
caggtgacca ccgccaagaa gctgcggggc ggcgtggtgt tcgtggacga ggtcccgaag    3420
ggcctgaccg ggaagctcga cgcccggaag atccgcgaga tcctgatcaa ggccaagaag    3480
ggcggcaaga tcgccgtgtg aggactagtt ataagactga ctagcccgat gggcctccca    3540
acgggccctc ctcccctcct tgcaccgaga ttaataaaaa aaaaaaaaaa aaaaaaaaa     3600 aaaaaaaaa aaaaaaaaa aaaaaaaaa aaaaaaaat gcatcccccc cccccccccc         3660
cccccccccc ccccaaagg ctcttttcag agccaccaga attcaagcgt gatacccgct     3720
tgctgaagag tcccgtgagg gacgaaattc tggggatact ctagaatcca tgatatctgt    3780 tagtttttt ctactagagt actagagtat ctgttagttt ttttctacta gagtactaga     3840
gtatctgtta gttttttct actagagtac tagagtatct gttagttttt ttctactaga    3900
gcatatgctt aagcagctgc attaatgaat cggccaacgc gcggggagag gcggtttgcg    3960
tattgggcgc tcttccgctt cctcgctcac tgactcgctg cgctcggtcg ttcggctgcg    4020
gcgagcggta tcagctcact caaaggcggt aatacggtta ccacagaat cagggataa     4080 cgcaggaaag aa                                                       4092

<210> SEQ ID NO 5
<211> LENGTH: 46
<212> TYPE: DNA
<213> ORGANISM: Artificial Sequence
<220> FEATURE:
<223> OTHER INFORMATION: 1xVSV

<400> SEQUENCE: 5
tctagaatcc atgatatctg ttagtttttt tctactagag catatg                   46

<210> SEQ ID NO 6
<211> LENGTH: 88
<212> TYPE: DNA
<213> ORGANISM: Artificial Sequence
<220> FEATURE:
<223> OTHER INFORMATION: 2x1R11

<400> SEQUENCE: 6
tctagatacc cctttcgtt ttatctgttt tttttggtg aacgtacccc ctttcgtttt      60
atctgttttt ttttggtgaa cgcatatg                                       88

<210> SEQ ID NO 7
```

```
<211> LENGTH: 148
<212> TYPE: DNA
<213> ORGANISM: Artificial Sequence
<220> FEATURE:
<223> OTHER INFORMATION: 4xVSV

<400> SEQUENCE: 7
tctagaatcc atgatatctg ttagttttttt tctactagag tactagagta tctgttagtt      60
tttttctact agagtactag agtatctgtt agtttttttc tactagagta ctagagtatc     120
tgttagtttt tttctactag agcatatg                                         148

<210> SEQ ID NO 8
<211> LENGTH: 73
<212> TYPE: DNA
<213> ORGANISM: Artificial Sequence
<220> FEATURE:
<223> OTHER INFORMATION: ribozyme-sequence 1

<400> SEQUENCE: 8
gaattccgtc taagcgtgat acccgcttac tgaagagtcc cgtgagggac gaaacggaat       60
tggatactct aga                                                         73

<210> SEQ ID NO 9
<211> LENGTH: 67
<212> TYPE: DNA
<213> ORGANISM: Artificial Sequence
<220> FEATURE:
<223> OTHER INFORMATION: ribozyme sequence 2

<400> SEQUENCE: 9
gaattcaagc gtgataccccg cttgctgaag agtcccgtga gggacgaaat tctggggata      60
ctctaga                                                                67

<210> SEQ ID NO 10
<211> LENGTH: 1870
<212> TYPE: RNA
<213> ORGANISM: Artificial Sequence
<220> FEATURE:
<223> OTHER INFORMATION: G/C optimized mRNA sequence coding for PpLuc

<400> SEQUENCE: 10
gggagaaagc uuaccaugga ggacgccaag aacaucaaga agggcccggc gcccuucuac       60
ccgcuggagg acgggaccgc cggcgagcag cuccacaagg ccaugaagcg guacgcccug      120
gugccgggca cgaucgccuu caccgacgcc cacaucgagg ucgacaucac cuacgcggag      180
uacuucgaga ugagcgugcg ccuggccgag gccaugaagc gguacggccu gaacaccaac      240
caccggaucg uggugugcuc ggagaacagc cugcaguucu ucaugccggu gcugggcgcc      300
cucuucaucg gcguggccgu cgccccggcg aacgacaucu acaacgagcg ggagcugcug      360
aacagcaugg gaucagcca gccgaccgug guguucguga gcaagaaggg ccugcagaag      420
auccugaacg ugcagaagaa gcugcccauc uccagaaga ucaucaucau ggacagcaag      480
accgacuacc agggcuucca gucgauguac acguucguga ccagccaccu cccgccgggc      540
uucaacgagu acgacuucgu cccggagagc uucgaccggg acaagaccau cgcccugauc      600
augaacagca gcggcagcac cggccugccg aaggggguggg cccugccgca ccggaccgcc      660
ugcgugcgcu ucucgcacgc ccgggacccc aucuucggca accagaucau cccggacacc      720
gccaucuuga gcgugguguc cguuccaccac ggcuucggca uguucacgac ccugggcuac      780
cucaucugcg gcuuccgggu gguccugaug uaccgguucg aggaggagcu guuccugcgg      840
```

```
agccugcagg acuacaagau ccagagcgcg cugcucgugc cgacccuguu cagcuucuuc    900
gccaagagca cccugaucga caaguacgac cugucgaacc ugcacgagau cgccagcggg    960
ggcgccccgc ugagcaagga ggugggcgag gccguggcca agcgguucca ccucccgggc   1020
auccgccagg gcuacggccu gaccgagacc acgagcgcga uccugaucac ccccgagggg   1080
gacgacaagc cgggcgccgu gggcaaggug gucccguucu ucgaggccaa ggugguggac   1140
cuggacaccg gcaagacccu gggcgugaac cagcggggcg agcugugcgu gcgggggccg   1200
augaucauga gcggcuacgu gaacaacccg gaggccacca cgcccucau cgacaaggac    1260 ggcuggcugc acagcggcga caucgccuac ugggacgagg acgagcacuu cuucaucguc   1320
gaccggcuga agucgcugau caaguacaag ggcuaccagg uggcgccggc cgagcuggag   1380
agcauccugu ccagcacccc aacaucuuc gacgccggcg uggccgggcu gccggacgac    1440
gacgccggcg agcugccggc cgcgguggug gugcuggagc acggcaagac caugacggag   1500
aaggagaucg ucgacuacgu ggccagccag gugaccaccg ccaagaagcu gcggggcggc   1560
gugguguucg uggacgaggu cccgaagggc cugaccggga agcucgacgc ccggaagauc   1620
cgcgagaucc ugaucaaggc caagaagggc ggcaagaucg ccgugugagg acuaguuaua   1680
agacugacua gcccgauggg ccucccaacg ggcccuccuc cccuccuugc accgagauua   1740
auaaaaaaaa aaaaaaaaaa aaaaaaaaaa aaaaaaaaaa aaaaaaaaaa aaaaaaaaaa   1800
aaaaaaugca ucccccccc cccccccccc cccccccccc ccaaaggcuc uuuucagagc    1860
caccagaauu                                                          1870

<210> SEQ ID NO 11
<211> LENGTH: 118
<212> TYPE: DNA
<213> ORGANISM: Artificial Sequence
<220> FEATURE:
<223> OTHER INFORMATION: fragment used for cloning p3-mod

<400> SEQUENCE: 11
aaaggctctt ttcagagcca ccagaattca agcgtgatac ccgcttgctg aagagtcccg    60
tgagggacga aattctgggg atactctaga atccatgata tctgttagtt ttttcta      118

<210> SEQ ID NO 12
<211> LENGTH: 26
<212> TYPE: DNA
<213> ORGANISM: Artificial Sequence
<220> FEATURE:
<223> OTHER INFORMATION: T7-CJ Class 2 terminator sequence

<400> SEQUENCE: 12
tgtgtcccta tctgttacag tctcct                                        26

<210> SEQ ID NO 13
<211> LENGTH: 26
<212> TYPE: DNA
<213> ORGANISM: Artificial Sequence
<220> FEATURE:
<223> OTHER INFORMATION: PTH Class 2 terminator sequence

<400> SEQUENCE: 13
atgcttgcca tctgttttct tgcaag                                        26

<210> SEQ ID NO 14
<211> LENGTH: 26
<212> TYPE: DNA
```

```
<213> ORGANISM: Artificial Sequence
<220> FEATURE:
<223> OTHER INFORMATION: VSV Class 2 terminator sequence

<400> SEQUENCE: 14
atccatgata tctgttagtt tttttc                                           26

<210> SEQ ID NO 15
<211> LENGTH: 30
<212> TYPE: DNA
<213> ORGANISM: Artificial Sequence
<220> FEATURE:
<223> OTHER INFORMATION: VSV-XhoI Class 2 terminator sequence

<400> SEQUENCE: 15
atccatgata tctgttctcg agttttttc                                        30

<210> SEQ ID NO 16
<211> LENGTH: 26
<212> TYPE: DNA
<213> ORGANISM: Artificial Sequence
<220> FEATURE:
<223> OTHER INFORMATION: rrnB T1 Class 2 terminator sequence

<400> SEQUENCE: 16
tttcgtttta tctgttgttt gtcgtg                                           26

<210> SEQ ID NO 17
<211> LENGTH: 26
<212> TYPE: DNA
<213> ORGANISM: Artificial Sequence
<220> FEATURE:
<223> OTHER INFORMATION: Adeno5 Class 2 terminator sequence

<400> SEQUENCE: 17
tagttttgta tctgttttgc agcagc                                           26

<210> SEQ ID NO 18
<211> LENGTH: 26
<212> TYPE: DNA
<213> ORGANISM: Artificial Sequence
<220> FEATURE:
<223> OTHER INFORMATION: (lambda P1) Class 2 terminator sequence

<400> SEQUENCE: 18
ttcgaacctc tctgtttact gataag                                           26

<210> SEQ ID NO 19
<211> LENGTH: 26
<212> TYPE: DNA
<213> ORGANISM: Artificial Sequence
<220> FEATURE:
<223> OTHER INFORMATION: T3-CJ Class 2 terminator sequence

<400> SEQUENCE: 19
atctctctgt gtccctatct gttagc                                           26

<210> SEQ ID NO 20
<211> LENGTH: 26
<212> TYPE: DNA
<213> ORGANISM: Artificial Sequence
<220> FEATURE:
<223> OTHER INFORMATION: K11-CJ Class 2 terminator sequence

<400> SEQUENCE: 20
atgtctctgt gtccctatct gttggt                                           26
```

<210> SEQ ID NO 21
<211> LENGTH: 38
<212> TYPE: DNA
<213> ORGANISM: Artificial Sequence
<220> FEATURE:
<223> OTHER INFORMATION: rrnC Class 2 terminator sequence

<400> SEQUENCE: 21
aaaatcatcc ttagcgaaag ctaaggattt tttttatc                              38

<210> SEQ ID NO 22
<211> LENGTH: 38
<212> TYPE: DNA
<213> ORGANISM: Artificial Sequence
<220> FEATURE:
<223> OTHER INFORMATION: 1W1 Class 2 terminator sequence

<400> SEQUENCE: 22
tacccccttt cgttttatct gttgtttgtc ggtgaacg                              38

<210> SEQ ID NO 23
<211> LENGTH: 38
<212> TYPE: DNA
<213> ORGANISM: Artificial Sequence
<220> FEATURE:
<223> OTHER INFORMATION: 1W2 Class 2 terminator sequence

<400> SEQUENCE: 23
tacccccttt cgttttatct gttgtttgtc ggggcccg                              38

<210> SEQ ID NO 24
<211> LENGTH: 38
<212> TYPE: DNA
<213> ORGANISM: Artificial Sequence
<220> FEATURE:
<223> OTHER INFORMATION: 1W3 Class 2 terminator sequence

<400> SEQUENCE: 24
tacccccttt cgttttatct gttgtttgtc gtttaaag                              38

<210> SEQ ID NO 25
<211> LENGTH: 38
<212> TYPE: DNA
<213> ORGANISM: Artificial Sequence
<220> FEATURE:
<223> OTHER INFORMATION: 2W1 Class 2 terminator sequence

<400> SEQUENCE: 25
tcgggtaccc cgttttatct gttgtttgtc ggtgaacg                              38

<210> SEQ ID NO 26
<211> LENGTH: 38
<212> TYPE: DNA
<213> ORGANISM: Artificial Sequence
<220> FEATURE:
<223> OTHER INFORMATION: 3W1 Class 2 terminator sequence

<400> SEQUENCE: 26
ctctagagtc cgttttatct gttgtttgtc ggtgaacg                              38

<210> SEQ ID NO 27
<211> LENGTH: 38
<212> TYPE: DNA
<213> ORGANISM: Artificial Sequence
<220> FEATURE:

<223> OTHER INFORMATION: 4W1 Class 2 terminator sequence

<400> SEQUENCE: 27
cctgcaggtc cgttttatct gttgtttgtc ggtgaacg                          38

<210> SEQ ID NO 28
<211> LENGTH: 38
<212> TYPE: DNA
<213> ORGANISM: Artificial Sequence
<220> FEATURE:
<223> OTHER INFORMATION: 2W7 Class 2 terminator sequence

<400> SEQUENCE: 28
tcgggtaccc cgttttatct gttgtttgtc gacctgca                          38

<210> SEQ ID NO 29
<211> LENGTH: 38
<212> TYPE: DNA
<213> ORGANISM: Artificial Sequence
<220> FEATURE:
<223> OTHER INFORMATION: 1I1 Class 2 terminator sequence

<400> SEQUENCE: 29
tacccccttt cgttccatct gttgtttgtc ggtgaacg                          38

<210> SEQ ID NO 30
<211> LENGTH: 38
<212> TYPE: DNA
<213> ORGANISM: Artificial Sequence
<220> FEATURE:
<223> OTHER INFORMATION: 1I3 Class 2 terminator sequence

<400> SEQUENCE: 30 taccccctttt cgttccatct gttgtttgtc gtttaaag                         38

<210> SEQ ID NO 31
<211> LENGTH: 38
<212> TYPE: DNA
<213> ORGANISM: Artificial Sequence
<220> FEATURE:
<223> OTHER INFORMATION: 1J1 Class 2 terminator sequence

<400> SEQUENCE: 31 taccccctttt cgttccatct gttctttctc ggtgaacg                         38

<210> SEQ ID NO 32
<211> LENGTH: 38
<212> TYPE: DNA
<213> ORGANISM: Artificial Sequence
<220> FEATURE:
<223> OTHER INFORMATION: 5K1 Class 2 terminator sequence

<400> SEQUENCE: 32
tcggtacccg cttgccatct gttgtttgtc ggtgaacg                          38

<210> SEQ ID NO 33
<211> LENGTH: 38
<212> TYPE: DNA
<213> ORGANISM: Artificial Sequence
<220> FEATURE:
<223> OTHER INFORMATION: 1N1 Class 2 terminator sequence

<400> SEQUENCE: 33 taccccctttt cgttttatct gttctttctc ggtgaacg                         38

```
<210> SEQ ID NO 34
<211> LENGTH: 38
<212> TYPE: DNA
<213> ORGANISM: Artificial Sequence
<220> FEATURE:
<223> OTHER INFORMATION: 1P10 Class 2 terminator sequence

<400> SEQUENCE: 34
tacccccttt cgttccatct gttttcttgc gacctgca                              38

<210> SEQ ID NO 35
<211> LENGTH: 38
<212> TYPE: DNA
<213> ORGANISM: Artificial Sequence
<220> FEATURE:
<223> OTHER INFORMATION: 5Q10 Class 2 terminator sequence

<400> SEQUENCE: 35
tcggtacccg cttgccatct gttttcttgc gacctgca                              38

<210> SEQ ID NO 36
<211> LENGTH: 38
<212> TYPE: DNA
<213> ORGANISM: Artificial Sequence
<220> FEATURE:
<223> OTHER INFORMATION: 1R11 Class 2 terminator sequence

<400> SEQUENCE: 36 taccccctttt cgttttatct gtttttttt ggtgaacg                              38

<210> SEQ ID NO 37
<211> LENGTH: 38
<212> TYPE: DNA
<213> ORGANISM: Artificial Sequence
<220> FEATURE:
<223> OTHER INFORMATION: 1S11 Class 2 terminator sequence

<400> SEQUENCE: 37 taccccctttt cgttccatct gtttttttt ggtgaacg                              38

<210> SEQ ID NO 38
<211> LENGTH: 39
<212> TYPE: DNA
<213> ORGANISM: Artificial Sequence
<220> FEATURE:
<223> OTHER INFORMATION: 3Y8 Class 2 terminator sequence

<400> SEQUENCE: 38
ctctagagtc cgttttatct gtttgtttgg acctgcagg                             39

<210> SEQ ID NO 39
<211> LENGTH: 39
<212> TYPE: DNA
<213> ORGANISM: Artificial Sequence
<220> FEATURE:
<223> OTHER INFORMATION: 4Y9 Class 2 terminator sequence

<400> SEQUENCE: 39
cctgcaggtc cgttttatct gtttgtttgg actctagag                             39

<210> SEQ ID NO 40
<211> LENGTH: 39
<212> TYPE: DNA
<213> ORGANISM: Artificial Sequence
<220> FEATURE:
<223> OTHER INFORMATION: 3Z8 Class 2 terminator sequence
```

```
<400> SEQUENCE: 40
ctctagagtc cgttttatct gttgttttgg acctgcagg                                        39
```